(12) United States Patent
Chen et al.

(10) Patent No.: US 12,391,914 B2
(45) Date of Patent: Aug. 19, 2025

(54) MICROFLUIDIC DEVICES FOR HIGH THROUGHPUT SCREENING OF CELL-CELL INTERACTIONS

(71) Applicant: Shennon Biotechnologies Inc., San Francisco, CA (US)

(72) Inventors: Yih Yang Chen, San Francisco, CA (US); Kaveh Milaninia, San Jose, CA (US); Li Sun, San Francisco, CA (US)

(73) Assignee: Shennon Biotechnologies Inc., San Francisco, CA (US)

( * ) Notice: Subject to any disclaimer, the term of this patent is extended or adjusted under 35 U.S.C. 154(b) by 0 days.

(21) Appl. No.: 18/793,237

(22) Filed: Aug. 2, 2024

(65) Prior Publication Data

US 2024/0392237 A1    Nov. 28, 2024

Related U.S. Application Data

(63) Continuation of application No. 18/503,723, filed on Nov. 7, 2023.
(Continued)

(51) Int. Cl.
*B01L 3/00* (2006.01)
*B01F 23/41* (2022.01)
(Continued)

(52) U.S. Cl.
CPC ............ *C12N 5/0012* (2013.01); *B01F 23/41* (2022.01); *B01L 3/502792* (2013.01); *C12N 11/04* (2013.01); *B01L 2400/02* (2013.01)

(58) Field of Classification Search
None
See application file for complete search history.

(56) References Cited

U.S. PATENT DOCUMENTS

| 6,592,821 B1 | 7/2003 | Wada et al. |
| 7,708,949 B2 | 5/2010 | Stone et al. |

(Continued)

FOREIGN PATENT DOCUMENTS

| CN | 102388145 A | 3/2012 |
| WO | 2004002627 A2 | 1/2004 |

(Continued)

OTHER PUBLICATIONS

Subedi et al., "An Automated Real-time Microfuldic Platform to Probe Single NK Cell Heterogeneity and Cytotoxicity On-chip," Sci. Rep. 11:17084 (2021).
(Continued)

*Primary Examiner* — Brian R Gordon
(74) *Attorney, Agent, or Firm* — Goodwin Procter LLP

(57) ABSTRACT

Disclosed are methods and microfluidic devices for successfully co-encapsulating two or more cells in a high-throughput, high efficiency manner. Cells are organized into two or more ordered streams flowing through separate microchannels of the microfluidic device. Cells in ordered streams are sufficiently spaced such that at a junction of the microfluidic device, single droplets are generated that include exactly one cell from the first ordered stream of cells and at least one cell from the second ordered stream of cells. Single droplets including two or more cells are useful for performing assays (e.g., high throughput cell-cell interaction assays).

18 Claims, 19 Drawing Sheets

Related U.S. Application Data

(60) Provisional application No. 63/423,233, filed on Nov. 7, 2022.

(51) Int. Cl.
  *C12N 5/00* (2006.01)
  *C12N 11/04* (2006.01)

(56) References Cited

U.S. PATENT DOCUMENTS

| | | |
|---|---|---|
| 8,337,778 B2 | 12/2012 | Stone et al. |
| 9,176,504 B2 | 11/2015 | Chiou et al. |
| 10,473,647 B1 | 11/2019 | Anderson |
| 2002/0061847 A1 | 5/2002 | Wheeler et al. |
| 2003/0207326 A1 | 11/2003 | Su et al. |
| 2004/0241759 A1 | 12/2004 | Tozer et al. |
| 2006/0023559 A1 | 2/2006 | Xu et al. |
| 2006/0163385 A1 | 7/2006 | Link et al. |
| 2007/0003442 A1 | 1/2007 | Link et al. |
| 2007/0065946 A1 | 3/2007 | Reboud et al. |
| 2008/0063634 A1 | 3/2008 | Salfeld et al. |
| 2009/0131543 A1 | 5/2009 | Weitz et al. |
| 2010/0068754 A1 | 3/2010 | Kirakossian |
| 2010/0092955 A1 | 4/2010 | Harriman |
| 2010/0120047 A1 | 5/2010 | Forsyth |
| 2010/0172803 A1 | 7/2010 | Stone et al. |
| 2011/0166027 A1* | 7/2011 | Weiner ............ G01N 33/54366 435/243 |
| 2011/0275063 A1 | 11/2011 | Weitz et al. |
| 2012/0004185 A1 | 1/2012 | Greene |
| 2012/0122714 A1 | 5/2012 | Samuels et al. |
| 2012/0149592 A1 | 6/2012 | Love et al. |
| 2014/0128276 A1 | 5/2014 | Li et al. |
| 2014/0338753 A1 | 11/2014 | Sperling et al. |
| 2015/0034620 A1 | 2/2015 | Zhang et al. |
| 2015/0190506 A1 | 7/2015 | Cheung et al. |
| 2015/0298091 A1 | 10/2015 | Weitz et al. |
| 2015/0346201 A1 | 12/2015 | Korny et al. |
| 2016/0146823 A1* | 5/2016 | Chiu ................. G01N 33/5304 506/9 |
| 2016/0187240 A1* | 6/2016 | Ismagilov ............ G05D 7/0694 436/180 |
| 2016/0201129 A1 | 7/2016 | Weitz et al. |
| 2017/0028365 A1 | 2/2017 | Link et al. |
| 2017/0128940 A1* | 5/2017 | Amini ................. B01F 33/3011 |
| 2017/0199173 A1 | 7/2017 | Konry et al. |
| 2018/0203005 A1* | 7/2018 | Konry ............. G01N 33/54346 |
| 2020/0086321 A1 | 3/2020 | Park et al. |
| 2020/0324288 A1* | 10/2020 | Lee ......................... C12M 21/00 |
| 2020/0376488 A1* | 12/2020 | Wu .................... G01N 15/1484 |
| 2022/0390436 A1* | 12/2022 | Srinivasan ............. C12M 23/16 |
| 2023/0250468 A1* | 8/2023 | Schoepp .............. C12Q 1/6804 435/6.11 |
| 2024/0182849 A1 | 6/2024 | Chen et al. |
| 2024/0359180 A1* | 10/2024 | Patno ................. B01L 3/502715 |

FOREIGN PATENT DOCUMENTS

| | | |
|---|---|---|
| WO | 2004091763 A2 | 10/2004 |
| WO | 2005021151 A1 | 3/2005 |
| WO | 2006096571 A2 | 9/2006 |
| WO | 2009011808 A1 | 1/2009 |
| WO | 2009020633 A2 | 2/2009 |
| WO | 2009026448 A1 | 2/2009 |
| WO | 2009120254 A1 | 10/2009 |
| WO | 2010005593 A1 | 1/2010 |
| WO | 2010085275 A1 | 7/2010 |
| WO | 2010151776 A2 | 12/2010 |
| WO | 2012167142 A2 | 12/2012 |
| WO | 2013095737 A2 | 6/2013 |
| WO | 2013126774 A2 | 8/2013 |
| WO | 2015031190 A1 | 3/2015 |
| WO | 2017165791 A1 | 9/2017 |

OTHER PUBLICATIONS

International Search Report for International Patent Application No. PCT/US23/78930, mailed Apr. 8, 2024, 4 pgs.

Written Opinion for International Patent Application No. PCT/US23/78930, mailed Apr. 8, 2024, 9 pgs.

Martel et al., "Inertial Focusing in Microfluids," Ann. Rev. Biomed. Eng. 16:371-396 (2014).

Lagus et al., "High-throughput Co-encapsulation of Self-ordered Cell Trains: Cell Pair Interactions in Microdroplets," RSC Adv. 3:20512-20522 (2013).

Brouzes et al., Droplet microfluidic technology for single-cell high-throughput screening, Proc. Natl. Acad. Sci. USA, 106(34):14195-14200 (2009).

Extended European Search Report mailed Apr. 24, 2017 for Application No. EP 14840425.4 (7 pages).

International Search Report and Written Opinion mailed Dec. 4, 2014 for Application No. PCT/US2014/052271 (11 pages).

International Search Report and Written Opinion mailed Jun. 16, 2017 for Application No. PCT/US2017/024058 (9 pages).

Konry et al., Droplet-based microfluidic platforms for single T cell secretion analysis of IL-10 cytokine. Biosens Bioelectron, 26(5):2707-2710 (2011).

Konry et al., Ultrasensitive Detection of Low-Abundance Surface-Marker Protein using Isothermal Rolling Circle Amplification in Microfluidic Nano-Liter Platform. Small. Jun. 27, 2012:1-10. Author manuscript.

Serganov A et al., Metabolic imaging: a link between lactate dehydrogenase A, lactate, and tumor phenotype. Clin. Cancer Res. 17(19):6250-6261 (2011).

Tumarkin et al., High-throughput combinatorial cell co-culture using microfluidics. Integr. Biol. (Camb) 3(6):653-662 (2011).

Yuan et al., Droplet encapsulation improves accuracy of immune cell cytokine capture assays, Lab Chip. 20(8):1513-1520 (2020).

* cited by examiner

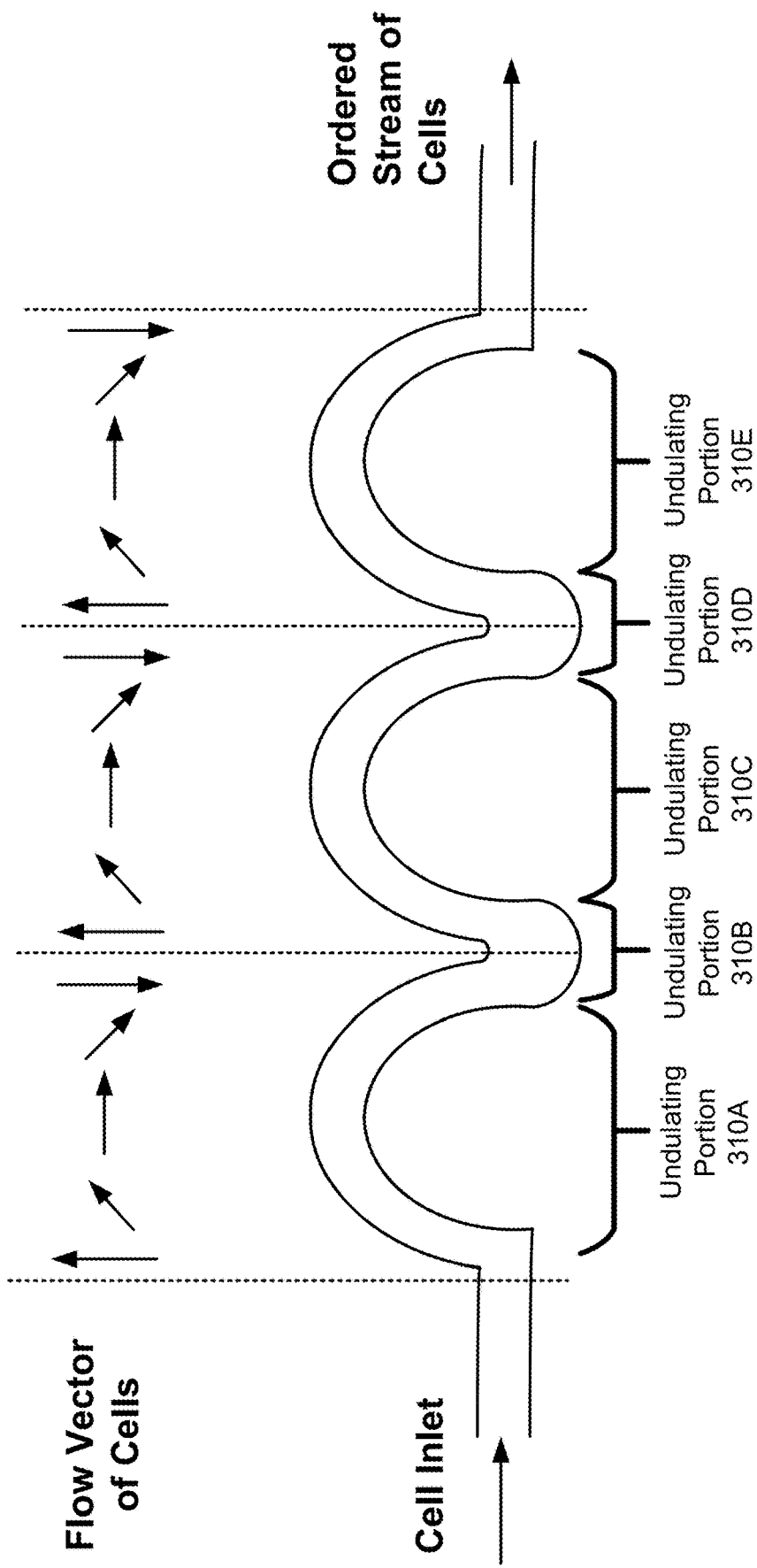

Example Flow around Pillars

MICROFLUIDIC DEVICES FOR HIGH THROUGHPUT SCREENING OF CELL-CELL INTERACTIONS

CROSS-REFERENCE TO RELATED APPLICATIONS

This application is a Continuation of U.S. application Ser. No. 18/503,723 filed Nov. 7, 2023, which claims the benefit of and priority to U.S. Provisional Patent Application No. 63/423,233 filed Nov. 7, 2022, the entire disclosure of each of which is hereby incorporated by reference in its entirety for all purposes.

BACKGROUND

Current high-throughput cell screening efforts focus on developing microfluidic devices for encapsulating single cells in single droplets. Thus, single cells are processed within the single droplets to generate data that can be traced back to the single cells. However, although encapsulation of single cells can be valuable for extracting data on a single-cell level, such single-cell data fails to capture cell-cell interactions (e.g., data pertaining to interactions between two or more cells).

SUMMARY

Disclosed herein are methods for generating single droplets from two or more ordered streams of cells, such that an improved proportion will contain one cell of the first ordered stream of cells, and at least one cell of the second ordered stream of cells. In various embodiments, a plurality of single droplets comprise a single cell from a first ordered stream and a single cell from a second ordered stream. In particular embodiments, the fraction of the plurality of single droplets that comprise a single cell from a first ordered stream and a single cell from a second ordered stream exceeds a predicted fraction predicted using a Poisson distribution.

Here, the disclosed methods enable the generation of such droplets in a high-throughput manner while achieving high efficiency and minimizing numbers of empty droplets. To generate single droplets that contain one cell from a first ordered stream and at least one cell from a second ordered stream in a high-throughput and efficient manner, the cells in the first ordered stream and the cells in the second ordered stream are organized and sufficiently spaced to achieve successful co-encapsulation. In various embodiments, cells in an ordered stream are lined up in a single file through a process known as inertial focusing caused by Dean forces. Inertial focusing pushes cells in a tangential direction to the direction of flow, until cells reach an equilibrium position. Once the cells of the ordered streams arrive at a droplet-generation zone, also referred to herein as a junction, of the microfluidic device, one cell from the first ordered stream of cells and at least one cell from the second ordered stream of cells are controllably encapsulated inside single droplets.

Notably, the generation of single droplets that encapsulate one cell from the first ordered stream of cells and at least one cell from the second ordered stream of cells cannot be accomplished by simply merging together two streams of ordered cells. In particular, the rate of inertial cell focusing increases with increasing flow velocity. However, increasing the flow velocity will prevent droplet generation due to the creation of "jetting" or "co-flow" regimes when the aqueous cell streams meet with the oil-phase sheath fluid. Thus, the addition of a second ordered stream of cells, which would be achieved by flowing the second stream fast enough to inertially focus the cells, will add too much aqueous flow velocity for droplet generation to occur. Conversely, if flow velocity is lowered to allow droplet generation, the cells in the ordered streams are not sufficiently inertially focused and therefore, fail to be controllably co-encapsulated in single droplets. Altogether, to achieve successful co-encapsulation of at least pairs of cells, various competing parameters are to be simultaneously tuned to achieve sufficient cell ordering and droplet co-encapsulation.

Disclosed herein is a method for encapsulating two cells in a single droplet, the method comprising: flowing a first aqueous phase comprising a first ordered stream of cells in a first microchannel towards a junction; flowing a second aqueous phase comprising a second ordered stream of cells in a second microchannel towards the junction; flowing an oil phase in a third microchannel towards the junction; and at the junction, generating the single droplet formed from the first aqueous phase, the second aqueous phase, and the oil phase, the single droplet comprising a cell from the first ordered stream of cells and a cell from the second ordered stream of cells. In various embodiments, methods disclosed herein further comprise: at the junction, further generating single droplets to generate a population of single droplets, wherein the population is characterized by a fraction of single droplets comprising a cell from the first ordered stream and a cell from the second ordered stream, and wherein the fraction exceeds a predicted fraction of single droplets comprising a cell from the first ordered stream and a cell from the second ordered stream predicted using a Poisson distribution. In various embodiments, the fraction exceeds the predicted fraction by a factor ranging from 2-3. In various embodiments, the method generates single droplets at a rate of at least 5,000 droplets per second. In various embodiments, the method generates single droplets at a rate of at least 8,000 droplets per second.

In various embodiments, cells of the first ordered stream of cells are aligned along a central axis or edge of the first microchannel. In various embodiments, cells of the first ordered stream of cells are aligned through inertial focusing while flowing through the first microchannel. In various embodiments, the inertial focusing is generated by flowing the first aqueous phase through a curved region of the first microchannel. In various embodiments, the curved region is between 150-300 mm in length. In various embodiments, the curved region is between 50-150 mm in length. In various embodiments, the curved region is about 100 mm in length. In various embodiments, the curved region comprises at least one undulating portion comprising at least a 45 degree change in a flow vector across a length of the undulating portion. In various embodiments, the curved region comprises at least one undulating portion comprising at least a 60 degree change, at least a 90 degree change, at least a 120 degree change, at least a 150 degree change, or at least a 180 degree change in a flow vector across a length of the undulating portion. In various embodiments, the curved region comprises between 60-120 undulating portions.

In various embodiments, an inter-cell spacing for at least 80% of cells in the first ordered stream is between 1 times an average cell diameter and 3.5 times an average cell diameter. In various embodiments, an inter-cell spacing for at least 60% of cells in the first ordered stream is between 1.5 times an average cell diameter and 3 times an average cell diameter. In various embodiments, a standard deviation of inter-cell spacing between pairs of successive cells is less than 10 μm when measured over 10, 20, 30, 40, 50, 60, 70, 80, 90, or 100 pairs of adjacent cells in the first ordered stream of cells. In various embodiments, the inter-cell spacing between pairs of cells in the first ordered stream of cells is modulated by passing the pairs of cells through a set of pillars. In various embodiments, the set of pillars is positioned at an entrance of the first microchannel. In various embodiments, the set of pillars at the entrance of the first microchannel comprise 5 to 40 µm gaps between pillars. In various embodiments, cells of the second ordered stream of cells are aligned along a central axis or edge of the second microchannel. In various embodiments, cells of the second ordered stream of cells are aligned through inertial focusing while flowing through the second microchannel. In various embodiments, the inertial focusing is generated by flowing the second aqueous phase through a curved region of the second microchannel. In various embodiments, the curved region of the second microchannel is between 150-300 mm in length. In various embodiments, the curved region is between 50-150 mm in length. In various embodiments, the curved region is about 100 mm in length. In various embodiments, the curved region of the second microchannel comprises at least one undulating portion comprising at least a 45 degree change in a flow vector across a length of the undulating portion. In various embodiments, the curved region of the second microchannel comprises at least one undulating portion comprising at least a 60 degree change, at least a 90 degree change, at least a 120 degree change, at least a 150 degree change, or at least a 180 degree change in a flow vector across a length of the undulating portion. In various embodiments, the curved region of the second microchannel comprises between 60-120 undulating portions. In various embodiments, an inter-cell spacing for at least 80% of cells in the second ordered stream is between 1 times an average cell diameter and 3.5 times an average cell diameter. In various embodiments, an inter-cell spacing for at least 60% of cells in the second ordered stream is between 1.5 times an average cell diameter and 3 times an average cell diameter. In various embodiments, a standard deviation of inter-cell spacing between pairs of successive cells is less than 10 µm when measured over 10, 20, 30, 40, 50, 60, 70, 80, 90, or 100 pairs of adjacent cells in the first ordered stream of cells.

In various embodiments, the inter-cell spacing between the pairs of cells in the second ordered stream of cells is modulated by passing the pairs of cells through a second set of pillars. In various embodiments, the second set of pillars is positioned at an entrance of the second microchannel. In various embodiments, the second set of pillars at the entrance of the second microchannel comprise 5 to 40 µm gaps between pillars.

In various embodiments, a ratio between a width of the first microchannel and an average diameter of cells in the first ordered stream of cells is between 1 and 20. In various embodiments, the ratio is between 1.5 and 10. In various embodiments, the ratio is between 1.5 and 7.5. In various embodiments, the ratio is between 2.5 and 5.0. In various embodiments, cells of the first ordered stream of cells are between 5-25 µm in diameter. In various embodiments, the first microchannel comprises a channel width between 10-100 µm. In various embodiments, a ratio between an average diameter of cells in the second ordered stream of cells and a width of the second microchannel is between 1 and 20. In various embodiments, the ratio is between 1.5 and 10. In various embodiments, the ratio is between 1.5 and 7.5. In various embodiments, the ratio is between 2.5 and 5.0. In various embodiments, cells of the second ordered stream of cells are between 5-25 µm in diameter. In various embodiments, the second microchannel comprises a channel width between 10-100 µm.

In various embodiments, a maximum concentration of cells $C_1$ in the first ordered stream of cells is defined according to:

$$C_1\left[\frac{\text{cells}}{\text{ml}}\right] = \frac{1[\text{cell}]}{(D_1 + S_1)[\text{m}] * W_1[\text{m}] * H_1[\text{m}]} * 10^{-6}\left[\frac{\text{m}^3}{\text{mL}}\right]$$

where $D_1$ represents diameter of cells of the first ordered stream, $S_1$ represents spacing between pairs of cells of the first ordered stream, $W_1$ represents width of first microchannel, and $H_1$ represents height of first microchannel.

In various embodiments, a maximum concentration of cells $C_2$ in the second ordered stream of cells is defined according to:

$$C_2\left[\frac{\text{cells}}{\text{ml}}\right] = \frac{1[\text{cell}]}{(D_2 + S_2)[\text{m}] * W_2[\text{m}] * H_2[\text{m}]} * 10^{-6}\left[\frac{\text{m}^3}{\text{mL}}\right]$$

where $D_2$ represents diameter of cells of the second ordered stream, $S_2$ represents spacing between pairs of cells of the second ordered stream, $W_2$ represents width of the second microchannel, and $H_2$ represents height of the second microchannel.

In various embodiments, wherein generating the single droplet comprises: contacting the flowing first aqueous phase and the second aqueous phase with one another, wherein the contacting creates a single aqueous phase comprising the first ordered stream of cells and the second ordered stream of cells. In various embodiments, the contacting of the flowing first aqueous phase and the second aqueous phase to create the single aqueous phase occurs at a location at or prior to the junction. In various embodiments, generating the single droplet further comprises: contacting the flowing oil phase with the single aqueous phase to form a cone configuration within the junction, wherein the single droplet is generated at a tip of the cone configuration.

In various embodiments, the cell from the first ordered stream of cells and the cell from the second ordered stream of cells are different types cells. In various embodiments, the cell from the first ordered stream of cells is a T-cell. In various embodiments, the cell from the second ordered stream of cells is an antigen presenting cell (APC). In various embodiments, the single droplet further comprises at least a second cell from the second ordered stream of cells. In various embodiments, the first aqueous phase is flowed at a first rate between 10 µL/min to 60 µL/min. In various embodiments, the first aqueous phase is flowed at a first rate of about 45 L/min. In various embodiments, the second aqueous phase is flowed at a second rate between 10 µL/min to 60 µL/min. In various embodiments, the second aqueous phase is flowed at a second rate of about 45 L/min. In various embodiments, the oil phase is flowed at a third rate between 10 µL/min to 60 µL/min. In various embodiments, the oil phase is flowed at a third rate of about 45 µL/min.

In various embodiments, the second aqueous phase is flowed at a second rate that is faster than a first rate of the first aqueous phase, such that the single droplet comprises only a single cell from the first ordered stream of cells and two or more cells from the second ordered stream of cells.

In various embodiments, methods disclosed herein further comprise: detecting an interaction between the cell from the first ordered stream of cells and the cell from the second ordered stream of cells. In various embodiments, the first aqueous phase or the second aqueous phase further comprise reagents for detecting the interaction. In various embodiments, the reagents comprise any of fluorescent markers, beads, or nucleic acid barcodes. In various embodiments, detecting the interaction comprises detecting a biomarker analyte indicative of the interaction. In various embodiments, the detecting the interaction comprises detecting the interaction within the single droplet.

Additionally disclosed herein is a method for encapsulating two or more cells in a plurality of droplets, the method comprising: flowing a first aqueous phase comprising a first ordered stream of cells in a first microchannel; flowing a second aqueous phase comprising a second ordered stream of cells in a second microchannel; flowing an oil phase in a third microchannel; and flowing together the first aqueous phase, the second aqueous phase, and the oil phase to generate the plurality of droplets, wherein at least 20% of droplets in the plurality of droplets include a single cell from the first ordered stream of cells and at least one cell from the second ordered stream of cells. In various embodiments, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of droplets in the plurality of droplets include a single cell from the first ordered stream of cells and at least one cell from the second ordered stream of cells.

In various embodiments, the plurality of droplets is characterized by a fraction of single droplets comprising a cell from the first ordered stream and a cell from the second ordered stream, and wherein the fraction exceeds a predicted fraction of single droplets comprising a cell from the first ordered stream and a cell from the second ordered stream predicted using a Poisson distribution. In various embodiments, the fraction exceeds the predicted fraction by a factor ranging from 2-3. In various embodiments, the method generates droplets of the plurality of droplets at a rate of at least 5,000 droplets per second. In various embodiments, the method generates droplets of the plurality of droplets at a rate of at least 8,000 droplets per second.

In various embodiments, cells of the first ordered stream of cells are aligned along a central axis of the first microchannel. In various embodiments, cells of the first ordered stream of cells are aligned through inertial focusing while flowing through the first microchannel. In various embodiments, the inertial focusing is generated by flowing the first aqueous phase through a curved region of the first microchannel. In various embodiments, the curved region is between 150-300 mm in length. In various embodiments, the curved region is between 50-150 mm in length. In various embodiments, the curved region is about 100 mm in length. In various embodiments, the curved region comprises at least one undulating portion comprising at least a 45 degree change in a flow vector across a length of the undulating portion. In various embodiments, the curved region comprises at least one undulating portion comprising at least a 60 degree change, at least a 90 degree change, at least a 120 degree change, at least a 150 degree change, or at least a 180 degree change in a flow vector across a length of the undulating portion. In various embodiments, the curved region comprises between 60-120 undulating portions.

In various embodiments, an inter-cell spacing for at least 80% of cells in the first ordered stream is between 1 times an average cell diameter and 3.5 times an average cell diameter. In various embodiments, an inter-cell spacing for at least 60% of cells in the first ordered stream is between 1.5 times an average cell diameter and 3 times an average cell diameter. In various embodiments, a standard deviation of inter-cell spacing between pairs of successive cells is less than 10 μm when measured over 10, 20, 30, 40, 50, 60, 70, 80, 90, or 100 pairs of adjacent cells in the first ordered stream of cells. In various embodiments, the inter-cell spacing between pairs of cells in the first ordered stream of cells is modulated by passing the pairs of cells through a set of pillars. In various embodiments, the set of pillars is positioned at an entrance of the first microchannel. In various embodiments, the set of pillars at the entrance of the first microchannel comprise 5 to 40 μm gaps between pillars.

In various embodiments, cells of the second ordered stream of cells are aligned along a central axis of the second microchannel. In various embodiments, cells of the second ordered stream of cells are aligned through inertial focusing while flowing through the second microchannel. In various embodiments, the inertial focusing is generated by flowing the second aqueous phase through a curved region of the second microchannel. In various embodiments, the curved region of the second microchannel is between 150-300 mm in length. In various embodiments, the curved region is between 50-150 mm in length. In various embodiments, the curved region is about 100 mm in length. In various embodiments, the curved region comprises at least one undulating portion comprising at least a 45 degree change in a flow vector across a length of the undulating portion. In various embodiments, the curved region comprises at least one undulating portion comprising at least a 60 degree change, at least a 90 degree change, at least a 120 degree change, at least a 150 degree change, or at least a 180 degree change in a flow vector across a length of the undulating portion. In various embodiments, the curved region comprises between 60-120 undulating portions. In various embodiments, an inter-cell spacing for at least 80% of cells in the second ordered stream is between 1 times an average cell diameter and 3.5 times an average cell diameter. In various embodiments, an inter-cell spacing for at least 60% of cells in the second ordered stream is between 1.5 times an average cell diameter and 3 times an average cell diameter. In various embodiments, a standard deviation of inter-cell spacing between pairs of successive cells is less than 10 μm when measured over 10, 20, 30, 40, 50, 60, 70, 80, 90, or 100 pairs of adjacent cells in the first ordered stream of cells. In various embodiments, the inter-cell spacing between pairs of cells in the second ordered stream of cells is modulated by passing the pairs of cells through a set of pillars. In various embodiments, the set of pillars is positioned at an entrance of the second microchannel. In various embodiments, the set of pillars at the entrance of the first microchannel comprise 5 to 40 μm gaps between pillars.

In various embodiments, a ratio between a width of the first microchannel and an average diameter of cells in the first ordered stream of cells is between 1 and 20. In various embodiments, the ratio is between 1.5 and 10. In various embodiments, the ratio is between 1.5 and 7.5. In various embodiments, the ratio is between 2.5 and 5.0. In various embodiments, cells of the first ordered stream of cells are between 5-25 μm in diameter. In various embodiments, the first microchannel comprises a channel width between 10-100 μm. In various embodiments, a ratio between an average diameter of cells in the second ordered stream of cells and a width of the second microchannel is between 1 and 20. In various embodiments, the ratio is between 1.5 and 10. In various embodiments, the ratio is between 1.5 and 7.5. In various embodiments, the ratio is between 2.5 and 5.0. In various embodiments, cells of the second ordered stream of cells are between 5-25 µm in diameter. In various embodiments, the second microchannel comprises a channel width between 10-100 µm.

In various embodiments, a maximum concentration of cells $C_1$ in the first ordered stream of cells is defined according to:

$$C_1 \left[\frac{\text{cells}}{\text{ml}}\right] = \frac{1 [\text{cell}]}{(D_1 + S_1)[m] * W_1[m] * H_1[m]} * 10^{-6} \left[\frac{m^3}{mL}\right]$$

where $D_1$ represents an average diameter of cells of the first ordered stream, $S_1$ represents spacing between pairs of cells of the first ordered stream, $W_1$ represents width of first microchannel, and $H_1$ represents height of first microchannel.

In various embodiments, a maximum concentration of cells $C_2$ in the second ordered stream of cells is defined according to:

$$C_2 \left[\frac{\text{cells}}{\text{ml}}\right] = \frac{1 [\text{cell}]}{(D_2 + S_2)[m] * W_2[m] * H_2[m]} * 10^{-6} \left[\frac{m^3}{mL}\right]$$

where $D_2$ represents an average diameter of cells of the first ordered stream, $S_2$ represents spacing between pairs of cells of the first ordered stream, $W_2$ represents width of first microchannel, and $H_2$ represents height of first microchannel.

In various embodiments, generating the single droplet comprises: contacting the flowing first aqueous phase and the second aqueous phase, wherein the contacting creates a single aqueous phase comprising the first ordered stream of cells and the second ordered stream of cells. In various embodiments, the contacting of the flowing first aqueous phase and the second aqueous phase to create the single aqueous phase occurs at a location at or prior to the junction. In various embodiments, generating the single droplet further comprises: contacting the flowing oil phase with the single aqueous phase to form a cone configuration within the junction, wherein the single droplet is generated at a tip of the cone configuration.

In various embodiments, the cell from the first ordered stream of cells and the cell from the second ordered stream of cells are different types cells. In various embodiments, the cell from the first ordered stream of cells is a T-cell. In various embodiments, the cell from the second ordered stream of cells is an antigen presenting cell (APC). In various embodiments, the single droplet further comprises at least a second cell from the second ordered stream of cells. In various embodiments, the first aqueous phase is flowed at a first rate between 10 µL/min to 60 µL/min. In various embodiments, the first aqueous phase is flowed at a first rate of about 45 µL/min. In various embodiments, the second aqueous phase is flowed at a second rate between 10 µL/min to 60 µL/min. In various embodiments, the second aqueous phase is flowed at a second rate of about 45 L/min. In various embodiments, the oil phase is flowed at a third rate between 10 µL/min to 60 µL/min. In various embodiments, the oil phase is flowed at a third rate of about 45 µL/min. In various embodiments, the second aqueous phase is flowed at a second rate that is faster than a first rate of the first aqueous phase, such that the single droplet comprises only a single cell from the first ordered stream of cells and two or more cells from the second ordered stream of cells.

In various embodiments, methods disclosed herein further comprise detecting an interaction within the single droplet between the cell from the first ordered stream of cells and the cell from the second ordered stream of cells. In various embodiments, the first aqueous phase or the second aqueous phase further comprise reagents for detecting the interaction. In various embodiments, the reagents comprise any of fluorescent markers, beads, or nucleic acid barcodes. In various embodiments, detecting the interaction within the single droplet comprises detecting a biomarker analyte indicative of the interaction.

Additionally disclosed herein is a a microfluidic device for encapsulating pairs of cells in droplets, the microfluidic device comprising: a first microchannel, a second microchannel, and a third microchannel, wherein the first microchannel, second microchannel and third microchannel are fluidically connected to one another through a junction, wherein the first microchannel comprises a curved region comprising a channel width between 10-100 µm, and wherein the second microchannel comprises a curved region comprising a channel width between 10-100 µm. In various embodiments, the curved region of the first microchannel and the curved region of the second microchannel are between 150-300 mm in length. In various embodiments, the first microchannel comprises a non-curved region, wherein the non-curved region is located proximal to the junction in comparison to the curved region of the first microchannel. In various embodiments, the second microchannel comprises a non-curved region, wherein the non-curved region is located proximal to the junction in comparison to the curved region of the second microchannel. In various embodiments, the channel width of the curved region of the first microchannel and wherein the channel width of the curved region of the second microchannel is between 15 and 75 µm. In various embodiments, a radius of curvature of the curved region of the first microchannel continuously increases along a full length of the curved region. In various embodiments, a radius of curvature of the curved region of the second microchannel continuously increases along a full length of the curved region. In various embodiments, a radius of curvature of the curved region of the first microchannel remains constant along a full length of the curved region. In various embodiments, the curved region of the first microchannel comprises a first undulating portion with a first radius of curvature and a second undulating portion with a second radius of curvature. In various embodiments, the first radius of curvature is different from the second radius of curvature. In various embodiments, the curved region comprises at least one undulating portion comprising at least a 45 degree change in a flow vector across a length of the undulating portion. In various embodiments, the curved region comprises at least one undulating portion comprising at least a 60 degree change, at least a 90 degree change, at least a 120 degree change, at least a 150 degree change, or at least a 180 degree change in a flow vector across a length of the undulating portion. In various embodiments, the curved region comprises between 60-120 undulating portions. In various embodiments, a radius of curvature of the curved region of the second microchannel remains constant along a full length of the curved region. In various embodiments, the curved region of the first microchannel comprises a first undulating portion with a first radius of curvature and a second undulating portion with a second radius of curvature.

In various embodiments, the first radius of curvature is different from the second radius of curvature. In various embodiments, the curved region comprises between 60-120 undulating portions. In various embodiments, the first microchannel further comprises a set of pillars positioned at an entrance of the first microchannel. In various embodiments, the set of pillars comprise 5 to 40 μm gaps between pillars. In various embodiments, the second microchannel further comprises a set of pillars positioned at an entrance of the second microchannel. In various embodiments, the set of pillars comprise 5 to 40 μm gaps between pillars.

BRIEF DESCRIPTION OF THE SEVERAL VIEWS OF THE DRAWINGS

These and other features, aspects, and advantages of the present invention will become better understood with regard to the following description and accompanying drawings. It is noted that wherever practicable similar or like reference numbers may be used in the figures and may indicate similar or like functionality. For example, a letter after a reference numeral, such as "aqueous well 105A," indicates that the text refers specifically to the element having that particular reference numeral. A reference numeral in the text without a following letter, such as "aqueous well 105," refers to any or all of the elements in the figures bearing that reference numeral (e.g. "aqueous well 105" in the text refers to reference numerals "aqueous well 105A" and/or "aqueous well 105B" in the figures).

FIGS. 3A and 3B depicts an example curved region of a serpentine microfluidic channel for ordering cells, in accordance with an embodiment.

DETAILED DESCRIPTION

Definitions

Figure 1A:
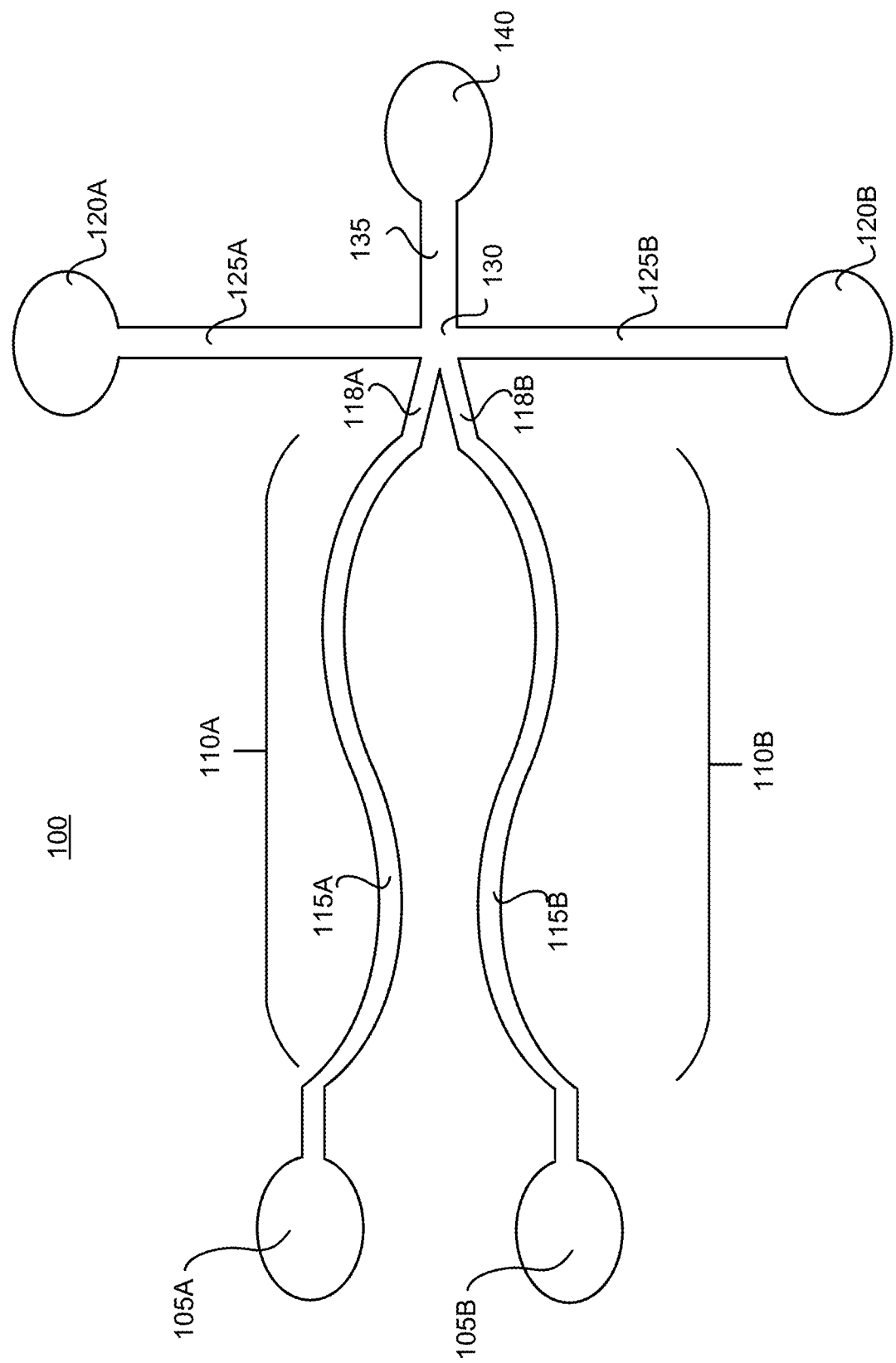
FIG. 1A shows an example schematic of a microfluidic device for encapsulating two or more cells in a single droplet, in accordance with an embodiment.

Terms used in the claims and specification are defined as set forth below unless otherwise specified.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

The term "subject" or "patient" are used interchangeably and encompass an organism, human or non-human, mammal or non-mammal, male or female.

In some embodiments, the discrete entities as described herein are droplets. The terms "emulsion," "drop," "droplet," and "microdroplet" are used interchangeably herein, to refer to small, generally spherically structures, containing at least a first fluid phase, e.g., an aqueous phase (e.g., water), bounded by a second fluid phase (e.g., oil) which is immiscible with the first fluid phase. In some embodiments, droplets according to the present disclosure may contain a first fluid phase, e.g., oil, bounded by a second immiscible fluid phase, e.g. an aqueous phase fluid (e.g., water). In some embodiments, the second fluid phase will be an immiscible phase carrier fluid. Thus droplets according to the present disclosure may be provided as aqueous-in-oil emulsions or oil-in-aqueous emulsions. Droplets may be sized and/or shaped as described herein for discrete entities. For example, droplets according to the present disclosure generally range from 1 μm to 1000 μm, inclusive, in diameter. Droplets according to the present disclosure may be used to encapsulate cells, nucleic acids (e.g., DNA), enzymes, reagents, reaction mixture, and a variety of other components. The term emulsion may be used to refer to an emulsion produced in, on, or by a microfluidic device and/or flowed from or applied by a microfluidic device.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art. Certain embodiments provide a plurality of droplets. In some embodiments, the plurality of droplets is formed from a first fluid, and may be substantially surrounded by a second fluid. As used herein, a droplet is "surrounded" by a fluid if a closed loop can be drawn around the droplet through only the fluid. A droplet is "completely surrounded" if closed loops going through only the fluid can be drawn around the droplet regardless of direction. A droplet is "substantially surrounded" if the loops going through only the fluid can be drawn around the droplet depending on the direction (e.g., in some cases, a loop around the droplet will comprise mostly of the fluid by may also comprise a second fluid, or a second droplet, etc.).

In most, but not all embodiments, the droplets and the fluid containing the droplets are substantially immiscible. In some cases, however, they may be miscible. In some cases, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc.

The phrase "at a junction" refers to a step that occurs at or within the vicinity of a microfluidic junction formed by the meeting of two or more microchannels. In various embodiments, "at a junction" refers to a step that occurs immediately downstream of a junction (e.g., within 1 mm, within 2 mm, within 3 mm, within 4 mm, or within 5 mm downstream of a junction). In particular embodiments, a junction is described herein in reference to droplet generation, and can be also referred to as a "droplet generation region."

The phrase "ordered stream of cells" refers to an alignment of flowing cells within a microfluidic channel. In some embodiments, a flowing stream of cells is an "ordered stream of cells" if a parallel line that is drawn relative to the direction of a flow vector of the cells successfully crosses through each cell in the flowing stream. In some embodiments, a flowing stream of cells is an "ordered stream of cells" if a parallel line that is drawn relative to the direction of a flow vector of the cells successfully crosses through at least 90%, at least 91%, at least 92%, at least 93%, at least 94%, at least 95%, at least 96%, at least 97%, at least 98%, or at least 99% of the cells in the flowing stream. In some embodiments, a flowing stream of cells is an "ordered stream of cells" if a line drawn parallel to the direction of a flow vector of the cells successfully crosses through the center of each cell in the flowing stream.

The phrase "average cell diameter" refers to the average e.g., mean diameter of a particular type of cell within an ordered stream of cells within a microfluidic channel. As further described herein, the average cell diameter can influence the inter-cell spacing between pairs of cells within an ordered stream of cells within a microfluidic channel.

Overview

Described herein are methods for ordering and co-encapsulating two or more cells in single droplets in a high-throughput and efficient manner. Methods can further involve studying interactions between the co-encapsulated two or more cells within the single droplets. Further disclosed herein are microfluidic systems for ordering streams of cells and co-encapsulating two or more cells in single droplets to study the interactions of the two or more cells. When the analyses are conducted in a high-throughput manner, such microfluidic systems can identify cells of interest while maintaining the integrity of these cells.

In various embodiments, methods for co-encapsulating two or more cells in single droplets in a high-throughput and efficient manner generally involve the following steps:
1. Ordering two streams of cells through curved regions of microchannels where the cells experience inertial focusing forces that result in the ordering of the cells (e.g., in an equilibrium of substantially equally distanced cells lined up in a single line in the microchannel)
2. Providing the two ordered streams of cells to a microchannel junction where they further encounter an oil phase. By tuning the speed of the oil phase, the oil phase cuts each of the cell streams by one cell distance, thereby resulting in co-encapsulation of a pair of cells, where one cell from a first ordered stream and a least one cell from a second ordered stream are in a single droplet.

Disclosed herein are methods for performing an assay in a single droplet comprising two cells, the method comprising: flowing a first aqueous phase comprising a first ordered stream of cells in a first microchannel towards a junction; flowing a second aqueous phase comprising a second ordered stream of cells in a second microchannel towards the junction; flowing an oil phase in a third microchannel towards the junction; and at the junction, generating the single droplet formed from the first aqueous phase, the second aqueous phase, and the oil phase, the single droplet comprising a cell from the first ordered stream of cells and a cell from the second ordered stream of cells. Additionally disclosed herein are methods for encapsulating pairs of cells in a plurality of droplets, the method comprising: flowing a first aqueous phase comprising a first ordered stream of cells in a first microchannel; flowing a second aqueous phase comprising a second ordered stream of cells in a second microchannel; flowing an oil phase in a third microchannel; and flowing together the first aqueous phase, the second aqueous phase, and the oil phase to generate the plurality of droplets. In various embodiments, the disclosed methods achieve a high co-encapsulation efficiency, wherein at least 15% of droplets in the plurality of droplets include a single cell from the first ordered stream of cells and a single cell from the second ordered stream of cells. In various embodiments, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of droplets in the plurality of droplets include a single cell from the first ordered stream of cells and a single cell from the second ordered stream of cells.

As described in further detail herein, a cell-cell interaction assay is performed on single droplets comprising two or more cells. For example, methods disclosed herein involve further encapsulating in the single droplets, during or after co-encapsulation, reagents for performing a cell-cell interaction assay. In a droplet where the two or more cells interact, the reagents report on the activation markers of the two or more cells and/or the secreted molecules in the environment. In various embodiments, methods disclosed herein further involve identifying or sorting cells of interest based on detection of the reagents.

Example Methods for Encapsulating Two Cells in a Single Droplet

Generally, methods for encapsulating two cells (or two more cells) in a single droplet involve at least two steps of 1) ordering two streams of cells in two separate microchannels, and 2) at a junction at which the two separate microchannels meet, generating the single droplet comprising a cell from the first ordered stream of cells and a cell from the second ordered stream of cells. As described herein, the parameters (e.g., concentration of cells in aqueous fluid, flow rate of aqueous phase including cells, flow rate of oil phase, microchannel width, and inter-cell spacing within an ordered stream of cells.) that are conducive for ordering cells into ordered streams may not be conducive for co-encapsulation of two or more cells into single droplets. Thus, the parameters are to be tuned to achieve a fluid flow regime that achieves both ordering of cell streams and co-encapsulation of two or more cells into a single droplet.

Generally, within a microfluidic device, the ordering of cells occurs within a curved region of a microchannel of the microfluidic device. Generally, the ordering of cells within a curved region of a microchannel is due to inertial focusing forces arising from the curvature of the curved region of the microchannel. These secondary forces cause secondary flow, also referred to as Dean flow. For example, under sufficient Dean flow, the equilibrium positions within a microchannel become unstable owing to the impingement of the secondary flow on particles. This can leave a single lateral equilibrium position within the microchannel e.g., at the inside wall of the curve, thereby causing cells to align in an ordered stream. Further details of cell ordering and Dean flow is described in Martel J M, et al. Inertial focusing in microfluidics. Annu Rev Biomed Eng. 2014 Jul. 11; 16:371-96, which is hereby incorporated by reference in its entirety.

The co-encapsulation of two or more cells into single droplets occurs at a junction of the microfluidic device. Generally, the junction represents the meeting of two or more microchannels, where a first microchannel and a second microchannel each carrying an ordered stream of cells (e.g., ordered as described above due to inertial focusing forces arising from curved regions of microchannels). Furthermore, at least one microchannel carrying an immiscible oil phase (immiscible relative to the aqueous fluid carrying the ordered stream of cells) flows to the junction. Thus, the meeting of the two or more microchannels carrying ordered streams of cells and the one or more microchannels carrying an immiscible oil phase results in the generation of single droplets that include two or more cells (e.g., one cell from a first ordered stream of cells and at least one cell from a second ordered stream of cells). Notably, the flow of the aqueous fluids carrying the ordered stream of cells and the flow of the immiscible oil phase are carefully controlled to avoid the entering into "jetting" or "co-flow" regimes in which droplet formation fails to occur.

Reference is now made to Figure (FIG. 1A, which shows an example schematic of a microfluidic device for encapsulating two or more cells in a single droplet, in accordance with an embodiment. FIG. 1A is shown for purposes of introducing a first aqueous well 105A, a second aqueous well 105B, a first microchannel 115A, a curved region 110A of the first microchannel 115A, a second microchannel 115B, a curved region 110B of the second microchannel 115B, a first oil phase well 120A, a third microchannel 125A fluidically connected to the first oil phase well 120A, a second oil phase well 120B, a fourth microchannel 125B fluidically connected to the second oil phase well 120B, a junction 130, a collection well 140, and a sixth microfluidic channel 135 fluidically connecting the junction 130 to the collection well 140. Generally, the operation of the microfluidic device shown in FIG. 1A involves flow solutions from the left (e.g., from wells 105A and 105B) towards the right (e.g., to the collection well 140).

Figure 6A:
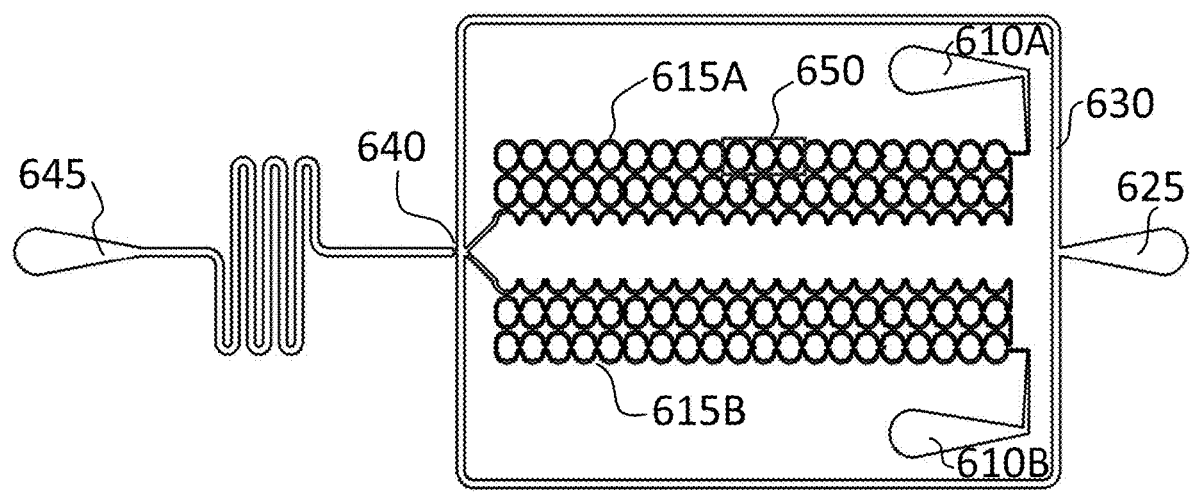
FIG. 6A depicts an example microfluidic device with serpentine microchannels.
Figure 7A:
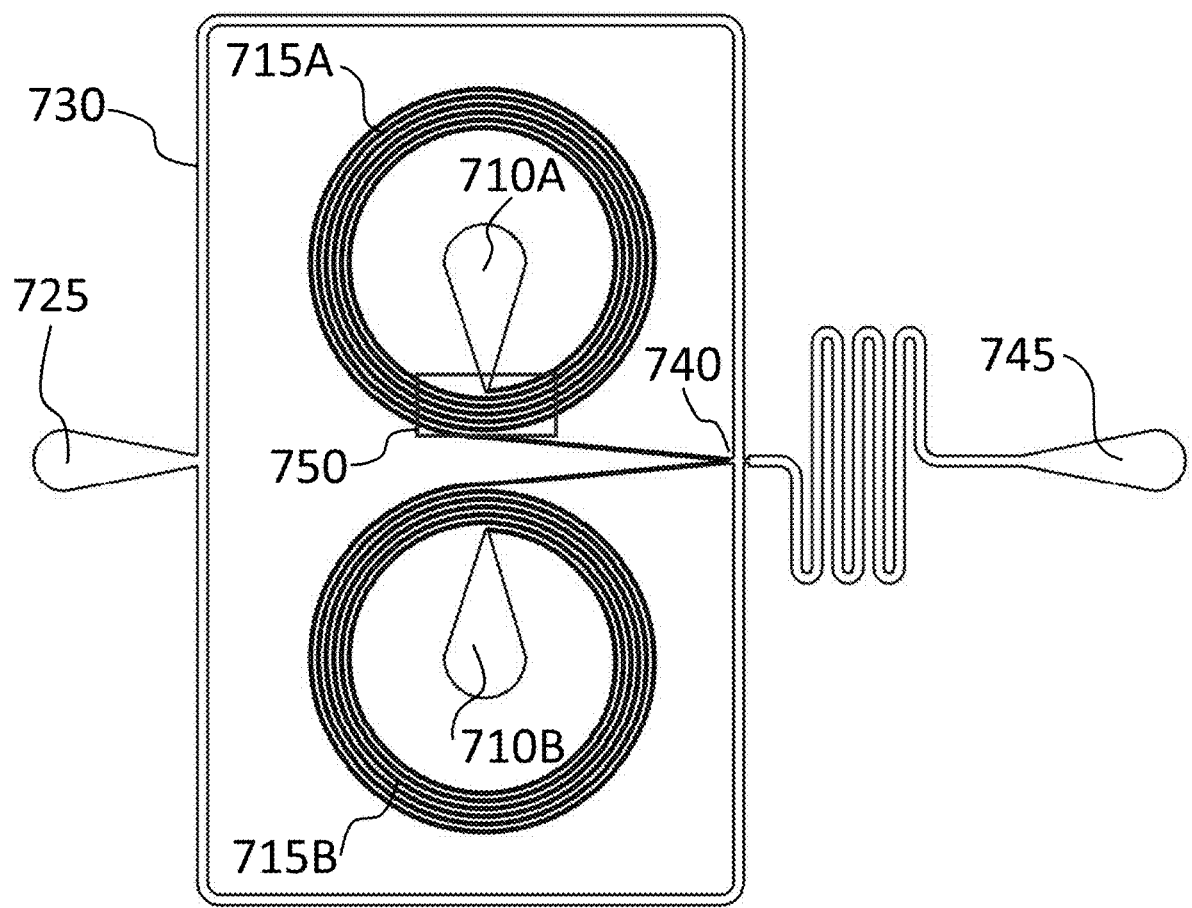
FIG. 7A depicts an example microfluidic device with spiral microchannels.

FIG. 1A shows one example embodiment of a microfluidic device for encapsulating two or more cells in a single droplet. In some embodiments, the device may be differently configured. As one example, the microfluidic device need not include two separate oil phase wells 120A and 120B and instead, includes a single oil phase well that is fluidically connected to provide the oil phase to the junction 130. Such example microfluidic devices are shown in FIG. 6A and FIG. 7A.

FIG. 1A shows two sets of an aqueous well 105, microchannel 115, and curved region 110 of microchannel 115 leading to the junction 130. In various embodiments, a microfluidic device may include additional sets of an aqueous well 105 connected to an additional microchannel 115 with a curved region 110. For example, a microfluidic device may include three sets, four sets, five sets, six sets, seven sets, eight sets, nine sets, or ten sets of an aqueous well 105 connected to an additional microchannel 115 with a curved region 110. This enables the co-encapsulation of various types of cells and/or reagents that are provided through the various aqueous wells that lead to the junction 130. For example, in various embodiments, a microfluidic device can enable co-encapsulation of two cells, three cells, four cells, five cells, six cells, seven cells, eight cells, nine cells, or ten or more cells within a single droplet.

Figure 9A:
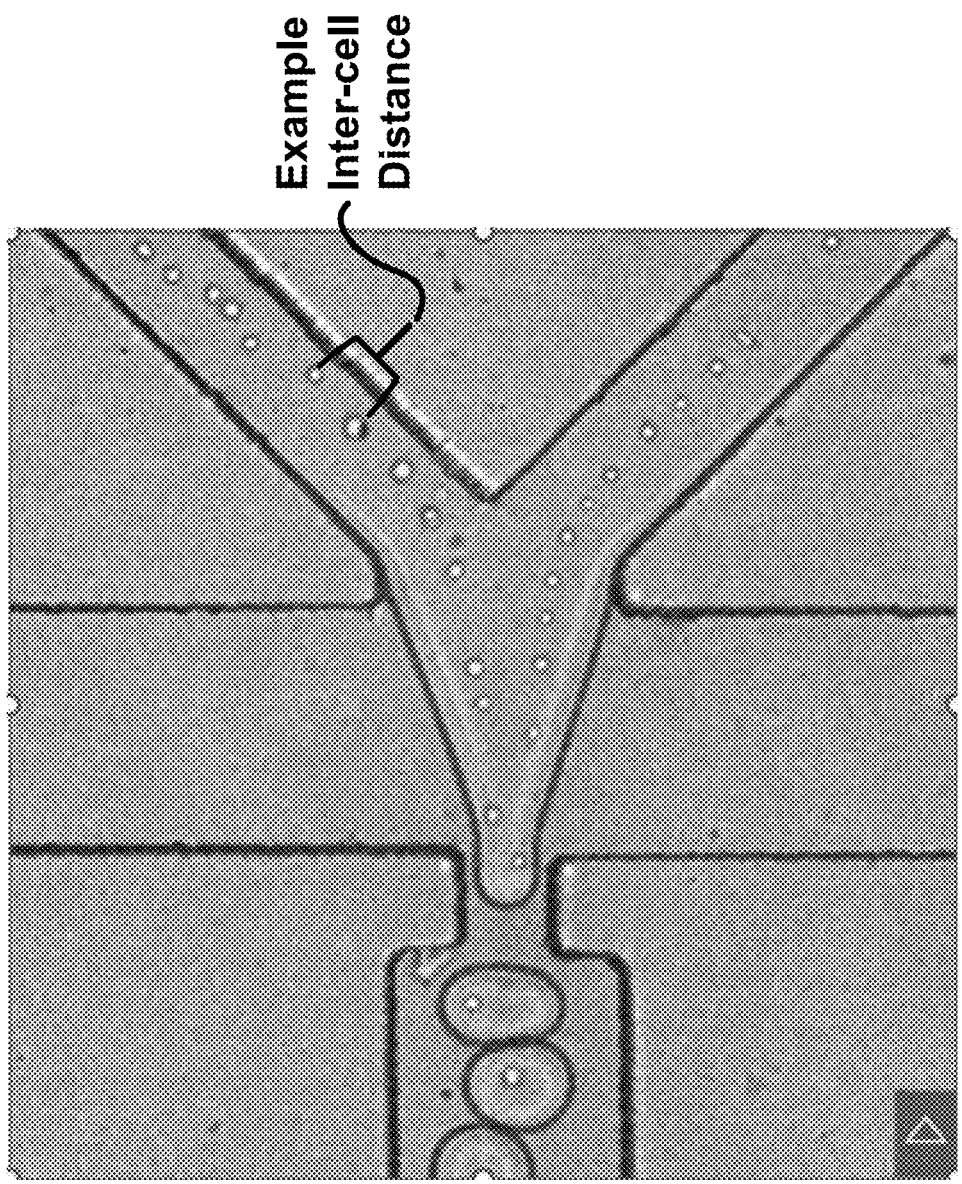
FIG. 9A shows an example bright-field image captured of two ordered streams of cells.

Generally, cells of a first cell type are provided to the first aqueous well 105A. Cells of a second cell type are provided to the second aqueous well 105B. Under microfluidic control, the cells of the first cell type are driven from the first aqueous well 105A through at least the curved region 110A of the first microchannel 115A. Here, the curved region 110A of the first microchannel 115A imparts inertial focusing forces on the cells of the first cell type to generate a first ordered stream of cells upon entering into the junction 130. Similarly, under microfluidic control, the cells of the second cell type are driven from the second aqueous well 105B through at least the curved region 110B of the second microchannel 115B. Here, the curved region 110B of the second microchannel 115B imparts inertial focusing forces on the cells of the second cell type to generate a second ordered stream of cells upon entering into the junction 130. For simple diagrammatic purposes, curved regions 110A and 110B are shown as serpentine portions of the first microchannel 115A and second microchannel 115B. However, as discussed in further detail herein (e.g., and as shown in FIGS. 6A and 9A), the curved regions 110A and 110B can be, in various embodiments, significantly more complicated.

Furthermore, as shown in FIG. 1A, the first channel 115A may include a non-curved region 118A leading up to the junction 130. Thus, the non-curved region 118A is located proximal to the junction 130 in comparison to the curved region 110A of the first microchannel 115A. Similarly, the second microchannel 115B may include a non-curved region 118B leading up to the junction 130. Thus, the non-curved region 118B is located proximal to the junction 130 in comparison to the curved region 110B of the second microchannel 115B. Here, the non-curved region 118A and 118B leading up the junction 130 enable the respective ordered stream of cells to approach the junction 130 while experiencing reduced, limited, or no inertial focusing forces.

Figure 1B:
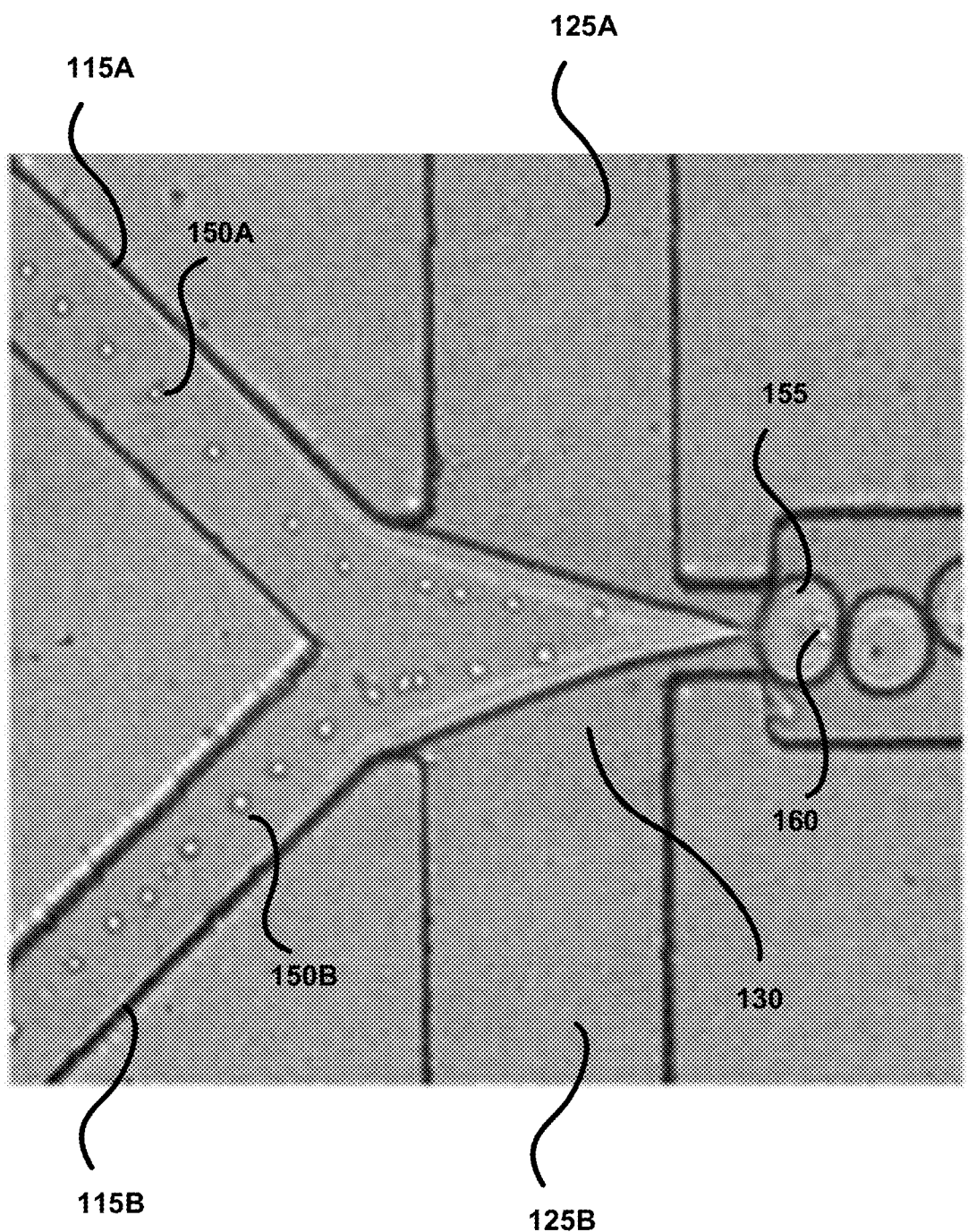
FIG. 1B shows a first ordered stream of cells, a second ordered stream of cells, and the encapsulation of two cells in a single droplet, in accordance with an embodiment.

An immiscible oil phase is provided to the oil phase well 120. Here, under microfluidic control, the oil phase flows through the third microchannel 125A and/or the fourth microchannel 125B to meet at the junction 130. Reference is now made to FIG. 1B, which shows a zoomed in view of the junction 130. In particular, FIG. 1B shows a first ordered stream of cells 150A entering the junction 130 through the first microchannel 115A, a second ordered stream of cells 150B entering the junction 130 through the second microchannel 115B, and the immiscible oil phases entering the junction 130 through the third microchannel 125A and the fourth microchannel 125B. The flowing aqueous fluids including the two ordered streams of cells are pinched by the flowing oil phases, thereby causing droplet formation downstream of the junction 130. Specifically, as shown in FIG. 1B, a single droplet 155 includes two or more cells 160, where one cell originates from the first ordered stream of cells 150A and another cell originates from the second ordered stream of cells 150B.

Example oil of an emulsion that is used as an immiscible oil phase can be selected based upon chemical properties e.g., molecular structure, content, solvating strength, viscosity, boiling point, thermal expansion coefficient, oil-in-water solubility, water-in-oil solubility, dielectric constant, polarity, water-in-oil surface tension, and/or oil-in-water surface tension. Examples of oils can include fluorinated oils, non-fluorinated oils, alkanes (e.g., hexane, decane, octane, and the like), mineral oils, plant oils, vegetable oils, comestible oils, mineral oil, oleic acid, embryo tested mineral oil, light mineral oil, heavy mineral oil, PCR mineral oil. AS4 silicone oil, AS 100 silicone oil, AR20 silicone oil, AR 200 silicone oil, AR 1000 silicone oil, AP 100 silicone oil, AP 1000 silicone oil, AP 150 silicone oil, AP 200 silicone oil, CR 200 Silicone oil, DC 200 silicone oil, DC702 silicone oil, DC 710 silicone oil, octanol, decanol, acetophenone, perfluoro-oils, perfluorononane, perfluorodecane, perfluorodimethyleylcohexane, perfluoro-1-butanesulfonyl fluoride, perfluoro-1-octanesulfonyl fluoride, perfluoro-1-octanesulfonyl fluoride, nonafluoro. 1-butanesulfonyl chloride, nonafluoro tert-butyl alcohol, perfluorodecanol, perfluorohexane, perfluorooctanol, perfluorodecene, perfluorohexene, perfluorooctene, fuel oil, halocarbon oil 28, halocarbon oil 700, hydrocarbon oil, glycerol, 3M Fluorinert™ fluids (FC-40, FC-43, FC-70, FC-72, FC-77, FC-84, FC-87, FC-3283), oils comprising trifluoroacetic acid, oils comprising hexafluoroisopropanol, Krytox oils (e.g., oils comprising hexafluoropropylene epoxide and/or polymers thereof), oil comprising polyhexafluoropropylene oxide and/or polymers thereof, Krytox GPL oils, oils comprising perfluoropolyether, oils comprising perfluoroalkylether, oils comprising perfluoropolyalkylether, Solvay Galden oils, oils including oils include hydrofluoroethers (e.g., HFE-7500, HFE-7100, HFE-7200, HFE-7600), oils comprising perfluoroalkylamines (e.g., Fluorinert FC-3283 and Fluorinert FC-40), soybean oil, castor oil, coconut oil, cedar oil, clove bud oil, fir oil, linseed oil, safflower oil, sunflower oil, almond seed oil, anise oil, clove oil, cottonseed oil, corn oil, croton oil, olive oil, palm oil, peanut oil, bay oil, borage oil, bergamot oil, cod liver oil, macadamia nut oil, camada oil, chamomile oil, citronella oil, eucalyptus oil, fennel oil, lavender oil, lemon oil, nutmeg oil orange oil, petitgrain oil, rose oil, tarragon oil, tung oil, basil oil, birch oil, black pepper oil, birch tar oil, carrot seed oil, cardamom oil, cassia oil, sage oil, cognac oil, copaiba balsam oil, cypress oil, eucalyptus oil, dillweed oil, grape fruit oil, ginger oil, juniper oil, lavender oil, lovage oil, majoram oil, mandarin oil, myrrh oil, neroli oil, olibanum oil, onion oil, paraffin oil, origanum oil, parsley oil, peppermint oil, pimenta leaf oil, sage oil, rosemary oil, rose oil, sandalwood oil, sassafras oil, spearmint oil, thyme oil, transformer oil, verbena oil, and rapeseed oil.

Returning to FIG. 1A, the droplets containing two or more cells continue to flow down the microchannel 135 towards a collection well 140. In various embodiments, while flowing through microchannel 135, the droplet can undergo an assay, such as a cell-cell interaction assay to interrogate whether the two or more cells interacted with each other. As described in further detail herein, the cell-cell interaction assay can involve capturing a signal (e.g., a fluorescent signal) emitted in a single droplet once a cell-cell interaction has occurred. Thus, in such embodiments, a detection module, i.e., a detector, e.g., an optical or fluorescent imager, can be configured to capture the signal emitted in single droplets. For example, the detection module can be situated to capture the signal emitted in single droplets while the droplets are flowing through microchannel 135 towards the collection well 140.

Figure 2:
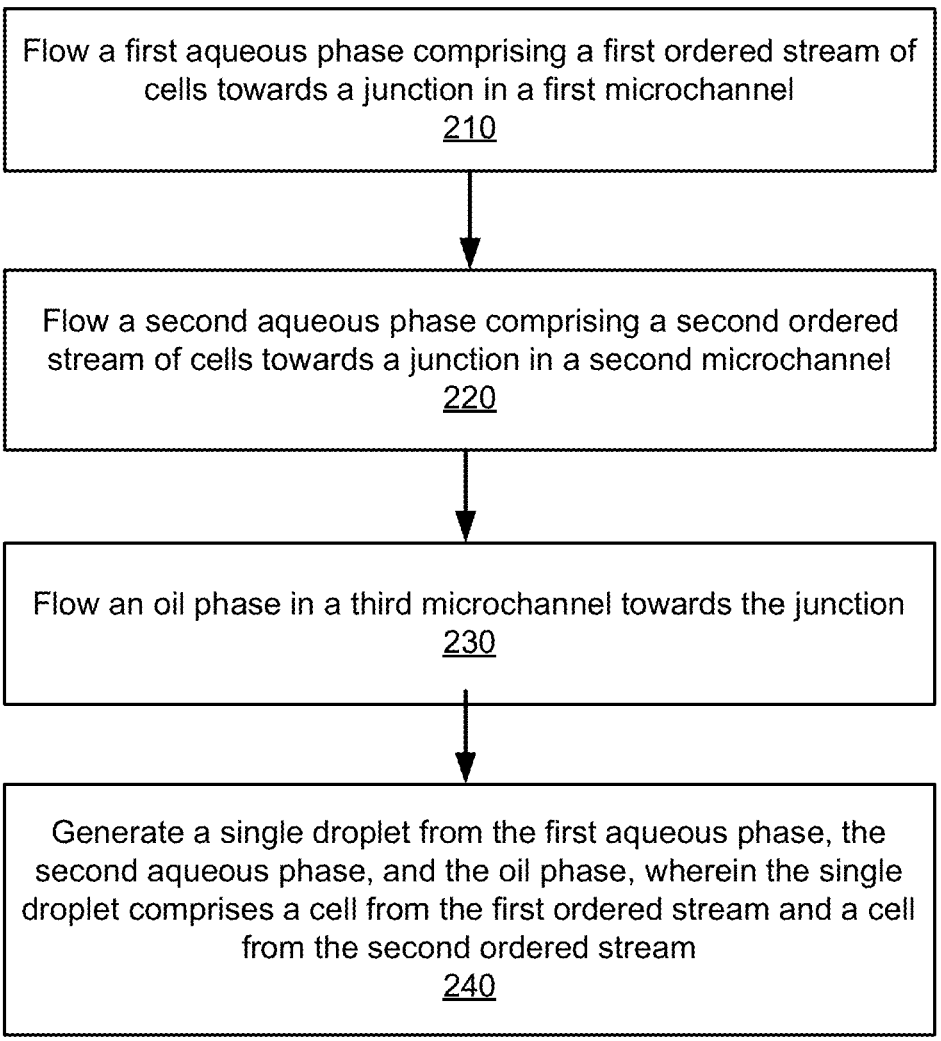
FIG. 2 depicts a flow diagram for ordering and encapsulating two cells into a single droplet, in accordance with an embodiment.

Reference is now made to FIG. 2, which depicts a flow diagram for ordering and encapsulating two cells into a single droplet, in accordance with an embodiment. As shown in FIG. 2, step 210 involves flowing a first aqueous phase comprising a first ordered stream of cells towards a junction in a first microchannel. Step 220 involves flowing a second aqueous phase comprising a second ordered stream of cells towards a junction in a second microchannel. Step 230 involves flowing an oil phase in a third microchannel towards the junction. Step 240 involves generating a single droplet from the first aqueous phase, the second aqueous phase, and the oil phase, wherein the single droplet comprises a cell from the first ordered stream and a cell from the second ordered stream.

Ordering Cells in a Stream

Embodiments described herein involve generating ordered streams of cells within microfluidic channels. In various embodiments, methods and apparati of the present disclosure involve generating two or more ordered streams of cells within two or more microfluidic channels. For example, embodiments may involve generating exactly two ordered streams of cells within two microfluidic channels. In other scenarios, embodiments may involve generating three ordered streams of cells within three microfluidic channels, four ordered streams of cells within four microfluidic channels, five ordered streams of cells within five microfluidic channels, six ordered streams of cells within six microfluidic channels, seven ordered streams of cells within seven microfluidic channels, eight ordered streams of cells within eight microfluidic channels, nine ordered streams of cells within nine microfluidic channels, or ten ordered streams of cells within ten microfluidic channels. As used herein, an "ordered stream of cells" refers to an alignment of flowing cells within a microfluidic channel. For example, a flowing stream of cells is an "ordered stream of cells" if a parallel line that is drawn relative to the direction of a flow vector of the cells successfully crosses through at least 90%, at least 91%, at least 92%, at least 93%, at least 94%, at least 95%, at least 96%, at least 97%, at least 98%, or at least 99% of the cells in the flowing stream.

Although the subsequent description is in reference to the ordering of cells within a single microchannel, the description can be similarly applied to the ordering of cells within multiple microchannels. Generally, cells in a microchannel are aligned into an ordered stream of cells through a process known as inertial focusing caused by Dean forces. Inertial focusing push cells in a tangential direction to the direction of flow, until cells reach an equilibrium position. In various embodiments, the equilibrium position may be along a central axis of the microchannel. Thus, in such embodiments, cells of an ordered stream of cells are aligned along the central axis of the microchannel. In various embodiments, the equilibrium position may not be along the central axis of the microchannel, and instead may be along a side or edge of the microchannel due to laminar fluid flow.

Generally, the inertial focusing due to secondary forces (e.g., Dean forces) arises due to the curvature of a microchannel (e.g., due to curved region 110A or curved region 110B shown in FIG. 1A). For example, Dean flow arises due to velocity differences in a microchannel cross section, such as in parabolic flow where the fluid in the center of a channel moves faster than fluid near the walls. The additional momentum carried by the faster-moving fluid in the center of a channel carries it toward the outer wall of the channel curvature as it enters a curve. Owing to conservation laws, this generates a recirculation of fluid toward the center of the channel curvature along top and bottom surfaces of the channel. Altogether, the implementation of a curved region within a microchannel imparts inertial focusing forces on flowing cells, thereby aligning the flowing cells to generate an ordered stream of cells within the microchannel.

In various embodiments, the curved region of a microfluidic channel includes at least an undulating portion in which the directional flow vector of cells changes over the length of the undulating portion. The change in the directional flow vector of the cells causes the imparting of inertial focusing forces on the flowing cells. In various embodiments, the curved region comprises at least one undulating portion comprising at least a 45 degree change in a flow vector across a length of the undulating portion. In various embodiments, the curved region comprises at least one undulating portion comprising at least a 60 degree change, at least a 90 degree change, at least a 120 degree change, at least a 150 degree change, or at least a 180 degree change in a flow vector across a length of the undulating portion.

Reference is now made to FIG. 3A which depicts an example curved region of a serpentine microfluidic channel for ordering cells, in accordance with an embodiment. For example, the curved region 115 shown in FIG. 3A may refer to curved region 115A or curved region 115B shown in FIG. 1A. FIG. 3A shows a serpentine microfluidic channel with multiple asymmetric curves. In particular, the flow of cells enters from the left side labeled as "Cell Inlet." The cells flow through multiple undulating portions (e.g., undulating portions 310A, 310B, 310C, 310D, and 310E). Following the flow through the undulating portions, which impart inertial focusing forces, the flowing cells exit to the right as an ordered stream of cells.

FIG. 3A also shows the directional flow vector of cells as they flow through the various undulating portions 310. Specifically, referring to the directional flow vector corresponding to undulating portion 310A, the flow vector begins at an upward 90° direction (assuming that a 0° direction is horizontally to the right). As the cells continue to flow through undulating portion 310A, the flow vector changes. For example, proceeding from the upward 90° direction, the flow vector decreases to 45°, then to 0°, then to −45°, and then to −90° at the end of undulating portion 310A. Referring to the directional flow vector corresponding to undulating portion 310B, the flow vector may begin at a downward −90° direction and then rapidly reverse to an upward 90° direction. The rapid directional flow change across the length of undulating portion 310B may further assist in the ordering of the stream of cells. As shown in FIG. 3A, the cells can further flow through undulating portions 310C and 310D, which may be duplicative of undulating portions 310A and 310B, respectively. Finally, the cells can further flow through undulating portion 310E, which may be duplicative of undulating portion 310A and/or undulating portion 310C.

Although FIG. 3A depicts five undulating portions in the asymmetrically curved microchannel, in various embodiments, there may be additional or fewer undulating portions in the curved region 115 of the microchannel. In various embodiments, the curved region 115 includes between 30 and 180 undulating portions. In various embodiments, the curved region 115 includes between 35 and 170 undulating portions, between 40 and 160 undulating portions, between 45 and 150 undulating portions, between 50 and 140 undulating portions, between 55 and 130 undulating portions, between 60 and 120 undulating portions, between 65 and 110 undulating portions, between 70 and 100 undulating portions, or between 75 and 90 undulating portions. In particular embodiments, the curved region 115 includes between 60 and 120 undulating portions.

Furthermore, FIG. 3A depicts two different undulating portions (e.g., undulating portion 310A and undulating portion 310B) that are then duplicated over the length of the curved region 115. Here, undulating portion 310A and undulating portion 310B may differ in that they have different radii of curvature. Specifically, undulating portion 310A may have a first radius of curvature that is larger than the radius of curvature of undulating portion 310B. Thus, as cells flow through the curved region 115, the cells experience different inertial focusing forces due to the first radius of curvature of the undulating portion 310A and the second radius of curvature of the undulating portion 310B. In various embodiments, undulating portion 310A and undulating portion 310B (as well as the duplicative undulating portions) have the same radius of curvature. Thus, in such embodiments, the radius of curvature of the curved region 115 of the microchannel may be constant across the full length of the curved region 115.

Figure 3B:
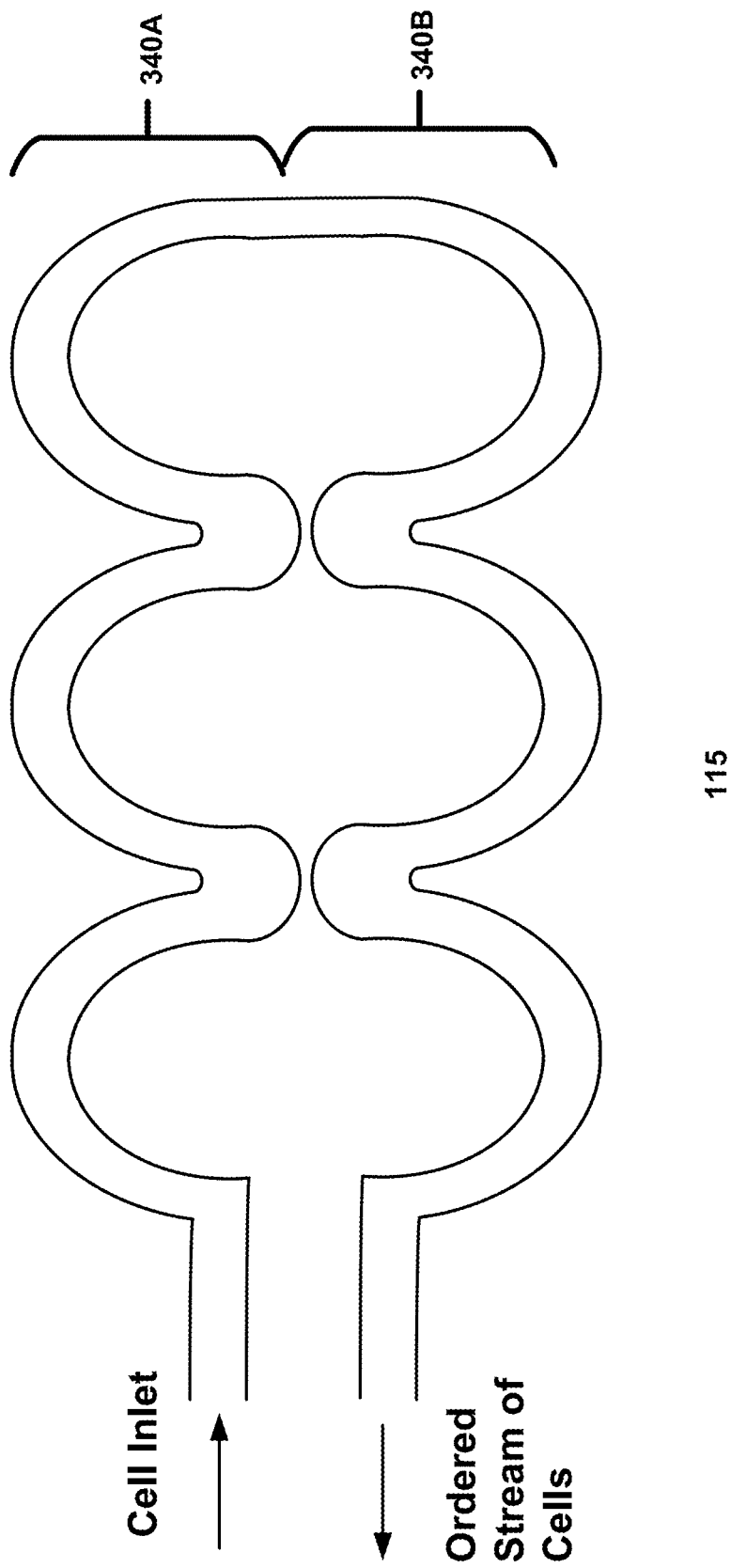

Reference is now made to FIG. 3B, which depicts an example curved region of a serpentine microfluidic channel for ordering cells, in accordance with a second embodiment. Here, the curved region 115 shown in FIG. 3B may include a unit 340A which includes the undulating portions 310 (e.g., 310A, 310B, 310C, 310D, and 310E) shown in FIG. 3A. Furthermore, curved region 115 shown in FIG. 3B may further include an additional unit 340B including additional undulating portions. Here, additional unit 340B may be a reflection of the undulating portions of the unit 340A. Thus, cells flow in from the top left, labeled as "cell inlet" through the undulating portions of the unit 340A and then continue to flow through the undulating portions of the unit 340B to the outlet, labeled as an "ordered stream of cells." Generally, the curved region 115 shown in FIG. 3B includes additional undulating portions in comparison to the curved region 115 shown in FIG. 3A, which means that cells flowing through the curved region 115 in FIG. 3B experience inertial focusing forces along the longer length of the curved portion 115 in FIG. 3B. The longer length of the curved region assists in consistent ordering of cells within the microchannel.

Figure 3C:
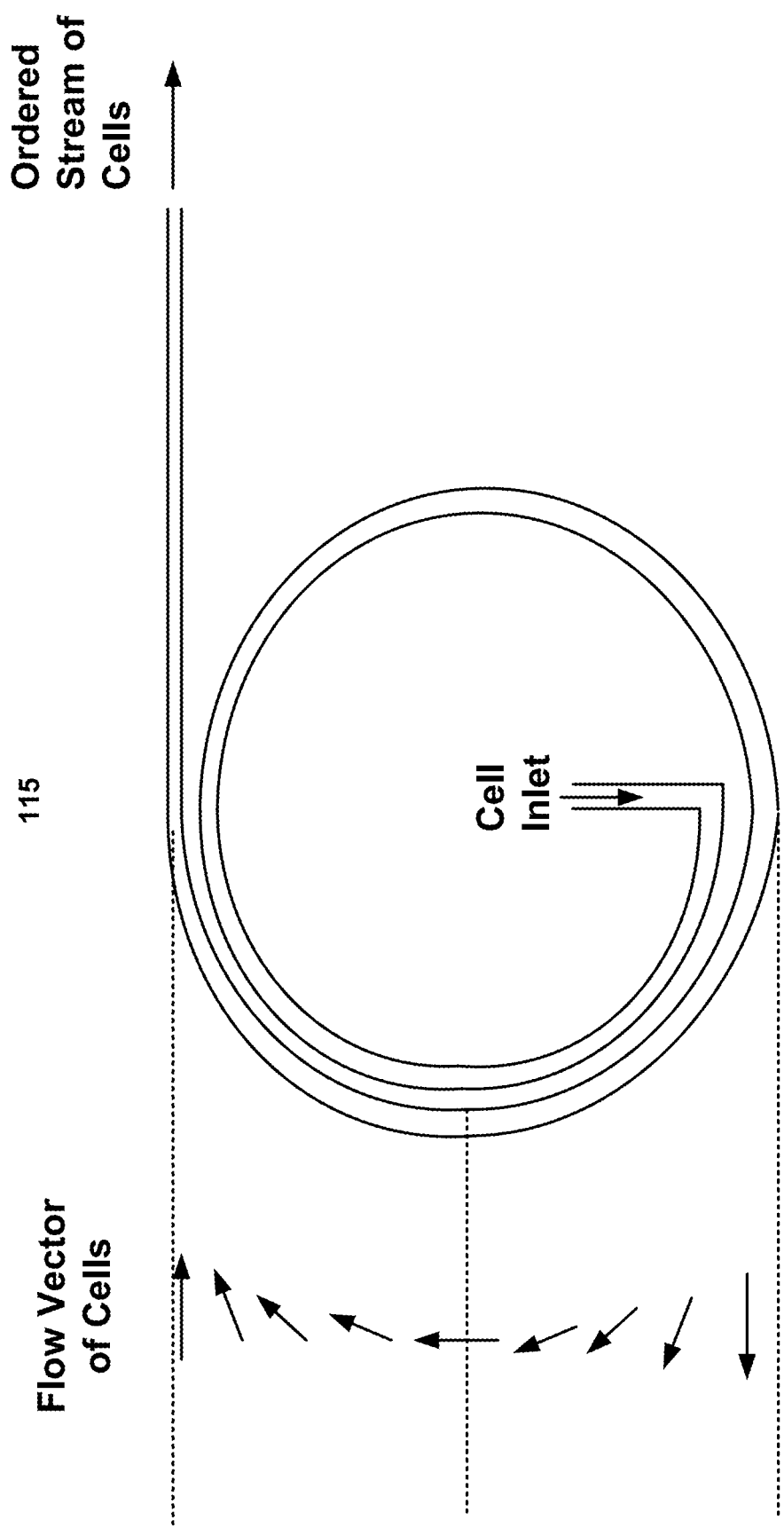
FIG. 3C depicts an example curved region of a spiral microfluidic channel for ordering cells, in accordance with an embodiment.

Reference is now made to FIG. 3C, which depicts an example curved region of a spiral microfluidic channel for ordering cells, in accordance with an embodiment. Generally, in a spiral microfluidic channel, inertial focusing forces increase as the radius of curvature in the microchannel decreases (e.g., a tighter curve of a microchannel creates a larger imbalance between the outward and inward forces, which preferentially pushes the cells towards the inside wall of the curve). As shown in FIG. 3C, the cell inlet can feed cells into the curved region 115. The radius of curvature of the curved region 115 increases with every loop, so inertial focusing becomes less efficient and flow resistance increases, which lowers overall flow velocity and further decreases inertial focusing. The equilibrium position for inertial focusing can be along the inner wall of the microchannel.

FIG. 3C depicts a spiral microfluidic channel with two loops (e.g., one interior loop and one exterior loop leading to the outlet labeled as "ordered stream of cells"). In various embodiments, the spiral microfluidic channel may include additional loops. For example, the spiral microfluidic channel may include three loops, four loops, five loops, six loops, seven loops, eight loops, nine loops, or ten loops before leading to the outlet. FIG. 3C further shows the directional flow vector of cells over a length of half of a loop. For example, beginning at the bottom portion of the loop, the directional flow vector is to the left (e.g., 180°). As the cells travel along the length of the channel, the flow vector continuously decreases from 180° to 135°, then to 90° at the halfway point, then to 45° and then to 0° before exiting through the outlet. Thus, over a half-length of a loop, the flow vector changes a full 180°. Furthermore, over a full length of a loop, the flow vector changes a full 360°.

In various embodiments, an ordered stream of cells includes 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more 18 or more 19 or more, 20 or more, 21 or more, 22 or more, 23 or more, 24 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 250 or more, 300 or more, 350 or more, 400 or more, 450 or more, 500 or more, 600 or more, 700 or more, 800 or more, 900 or more, 1000 or more, 1200 or more, 1500 or more, 1800 or more, 2000 or more, 2500 or more, 3000 or more, 4000 or more, 5000 or more, 10,000 or more, 15,000 or more, 20,000 or more, 25,000 or more, 30,000 or more, 40,000 or more, 50,000 or more, 100,000 or more, 200,000 or more, 300,000 or more, 400,000 or more, 500,000 or more, or 1 million or more cells. In particular embodiments, an ordered stream of cells include between 10 and 1000 cells, between 20 and 900 cells, between 30 and 800 cells, between 40 and 700 cells, between 50 and 600 cells, between 60 and 500 cells, between 70 and 400 cells, between 80 and 300 cells, between 90 and 200 cells, or between 100 and 150 cells.

As described herein, the inter-cell spacing refers to the distance between any pair of cells (e.g., center of a first cell and a center of a second cell) in the ordered stream. In particular embodiments, the inter-cell spacing refers to the distance between two successive cells (e.g., no other cell is present between the two successive cells) in the ordered stream. The inter-cell spacing may be described in relation to a cell diameter, such as an average cell diameter of cells in the ordered stream. In various embodiments, the inter-cell spacing between any pair of successive cells is between 0.5 times an average cell diameter and 5.5 times an average cell diameter. In particular embodiments, the inter-cell spacing between any pair of successive cells is between 1 times an average cell diameter and 5 times an average cell diameter, between 1.2 times an average cell diameter and 4 times an average cell diameter, between 1.5 times an average cell diameter and 3.5 times an average cell diameter, between 2 times an average cell diameter and 3 times an average cell diameter. In particular embodiments, the inter-cell spacing between any pair of successive cells is about 1 cell diameter, about 2 cell diameters, about 3 cell diameters, about 4 cell diameters, or about 5 cell diameters. In various embodiments, the cell diameter (e.g., average cell diameter) of cells is from about 5 μm to about 25 μm. Further example cell diameters are disclosed herein.

In various embodiments, for an ordered stream of cells, the inter-cell spacing for at least 80% of cells in the ordered stream is between 1 times an average cell diameter and 3.5 times an average cell diameter. In various embodiments, for an ordered stream of cells, the inter-cell spacing for at least 60% of cells in the ordered stream is between 1.5 times an average cell diameter and 3 times an average cell diameter. In various embodiments, for an ordered stream of cells, a standard deviation of inter-cell spacing between pairs of successive cells is less than 10 μm when measured over 10 pairs of adjacent cells in the first ordered stream of cells. In various embodiments, for an ordered stream of cells, a standard deviation of inter-cell spacing between pairs of successive cells is less than 10 μm when measured over 20, 30, 40, 50, 60, 70, 80, 90, or 100 pairs of adjacent cells in the first ordered stream of cells. In various embodiments, for an ordered stream of cells, a standard deviation of inter-cell spacing between pairs of successive cells is less than 9 μm, less than 8 μm, or less than 7 μm when measured over 20, 30, 40, 50, 60, 70, 80, 90, or 100 pairs of adjacent cells in the first ordered stream of cells.

Parameters for Ordering of Cells

As described herein, tunable parameters are set to achieve ordering of cells and successful co-encapsulation of two or more cells in single droplets. Example tunable parameters include: concentration of cells in aqueous fluid, flow rate of aqueous phase including cells, flow rate of oil phase, microchannel width, and inter-cell spacing within an ordered stream of cells. Disclosed herein are example sets of parameters that are conducive for ordering streams of cells and/or co-encapsulating two or more cells in single droplets.

Microfluidic Channel Dimensions and Cell Diameter

Generally, the successful ordering of cells into a stream can be dependent on the microfluidic channel width as well as the concentration of the cells. For example, as the microchannel width is widened, the maximum concentration of cells that can be processed decreases. Conversely, if the microchannel width is decreased, flow resistance increases, thereby limiting the volume of cell solution that can be processed per unit time. Therefore, microchannel width should be optimized to allow for maximum volume throughput and maximum cell concentration.

The description below refers to a single microchannel; however, one skilled in the art would understand that the description can refer to either or both of the microchannels (e.g., first microchannel 115A and/or second microchannel 115B) as described in FIG. 1A. In various embodiments, the appropriate width of a curved region of a microchannel (e.g., first microchannel and/or second microchannel) for ordering a stream of cells is dependent on the diameter of the cells. The diameter of the cells can refer to an average cell diameter of cells in the population of cells. In various embodiments, the width of a microchannel (e.g., a curved region of a microchannel) for ordering a stream of cells is from about 1 times the cell diameter to about 20 times the cell diameter. Put another way, a ratio between a width of the microchannel and an average diameter of cells in an ordered stream of cells is between 1 and 20. In various embodiments, the width of a microchannel (e.g., a curved region of a microchannel) for ordering a stream of cells is from about 2 times the cell diameter to about 8 times the cell diameter, from about 3 times the cell diameter to about 7 times the cell diameter, or from about 4 times the cell diameter to about 6 times the cell diameter. In various embodiments, the width of microchannel (e.g., a curved region of a microchannel) for ordering a stream of cells is about 1 times, about 1.5 times, about 2 times, about 2.5 times, about 3 times about 3.5 times, about 4 times, about 4.5 times, about 5 times, about 5.5 times, about 6 times, about 6.5 times, about 7 times, about 7.5 times, about 8 times, about 8.5 times, about 9 times, about 9.5 times, about 10 times, about 11.5 times, about 12 times, about 12.5 times, about 13 times, about 13.5 times, about 14 times, about 14.5 times, about 15 times, about 15.5 times, about 16 times, about 16.5 times, about 17 times, about 17.5 times, about 18 times, about 18.5 times, about 19 times, about 19.5 times, or about 20 times the cell diameter. In particular embodiments, a ratio between a width of the microchannel and an average diameter of cells in an ordered stream of cells is between 1.5 and 7.5. In particular embodiments, a ratio between a width of the microchannel and an average diameter of cells in an ordered stream of cells is between 2.5 and 5.0. In particular embodiments, a ratio between a width of the microchannel and an average diameter of cells in an ordered stream of cells is between 10.0 and 20.0, such as between 11.0 and 19.0, between 12.0 and 18.0, between 13.0 and 17.0, or between 14.0 and 16.0.

In various embodiments, the cell diameter (e.g., average cell diameter of a population of cells that undergo ordering) of cells is from about 5 µm to about 25 µm. In various embodiments, the cell diameter (e.g., average cell diameter of a population of cells that undergo ordering) of cells is from about 6 µm to about 24 µm, from about 7 µm to about 23 µm, from about 8 µm to about 22 µm, from about 9 µm to about 21 µm, from about 10 µm to about 20 µm, from about 11 µm to about 19 µm, from about 12 µm to about 18 µm, from about 13 µm to about 17 µm, or from about 14 µm to about 16 µm. In various embodiments, the cell diameter (e.g., average cell diameter of a population of cells that undergo ordering) of cells is about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 21 µm, about 22 µm, about 23 µm, about 24 µm, or about 25 µm.

In various embodiments, the width of a microchannel (e.g., first microchannel and/or second microchannel) is between from about 5 µm to about 200 µm. In various embodiments, the width of a microchannel is between from about 10 µm to about 100 µm, between from about 15 µm to about 95 µm, between from about 20 µm to about 90 µm, between from about 25 µm to about 85 µm, between from about 30 µm to about 80 µm, between from about 35 µm to about 75 µm, between from about 40 µm to about 70 µm, between from about 45 µm to about 65 µm, between from about 50 µm to about 60 µm. In various embodiments, the width of a microchannel is between from about 50 µm to about 100 µm (e.g., between from about 55 µm to about 95 µm, between from about 60 µm to about 90 µm, between from about 65 µm to about 85 µm, or between from about 70 µm to about 80 µm). In various embodiments, the width of a microchannel is between from about 50 µm to about 75 µm In particular embodiments, the width of a microchannel is about 50 µm. In particular embodiments, the width of a microchannel is about 75 µm. In various embodiments, a single microchannel can change in width, which further facilitates the ordering of cells into a stream. For example, a first portion of a single microchannel can have a width of about 50 µm, and a second portion of the single microchannel can have a width of about 75 µm.

Another tunable parameter includes the microchannel length. Specifically, the length of the curved region of a microchannel (e.g., first microchannel and/or second microchannel) can be tuned to allow more time for the Dean forces to inertially focus the cells. However, increasing the length of the curved region of a microchannel (e.g., first microchannel and/or second microchannel) will also increase flow resistance, and decreases flow velocity.

In various embodiments, the length of a curved region of a microchannel (e.g., first microchannel and/or second microchannel) is between from about 10 mm to about 500 mm. In various embodiments, the length of a curved region of a microchannel (e.g., first microchannel and/or second microchannel) is between from about 125 mm to about 400 mm, between from about 150 mm to about 300 mm, or between from about 175 mm to about 200 mm. In various embodiments, the length of a curved region of a microchannel (e.g., first microchannel and/or second microchannel) is between from about 100 mm to about 300 mm, between from about 125 mm to about 275 mm, between from about 150 mm to about 250 mm, between from about 175 mm to about 225 mm, between from about 180 mm to about 220 mm, between from about 185 mm to about 215 mm, between from about 190 mm to about 210 mm, or between from about 195 mm to about 205 mm. In various embodiments, the length of a curved region of a microchannel (e.g., first microchannel and/or second microchannel) is between from about 30 mm to about 400 mm, between from about 40 mm to about 350 mm, or between from about 50 mm to about 300 mm. In various embodiments, the length of a curved region of a microchannel (e.g., first microchannel and/or second microchannel) is between from about 40 mm to about 200 mm, between from about 50 mm to about 150 mm, between from about 60 mm to about 140 mm, between from about 70 mm to about 130 mm, between from about 80 mm to about 120 mm, between from about 85 mm to about 115 mm, between from about 90 mm to about 110 mm, or between from about 95 mm to about 105 mm. In various embodiments, the length of a curved region of a microchannel (e.g., first microchannel and/or second microchannel) is about 100 mm.

Cell Concentration

Generally, cell concentration is a tunable parameter for influencing the ordering of a stream of cells. For example, providing too low of a cell concentration can result in too low or slow of a throughput analysis. On the contrary, using too high of a cell concentration will cause cell aggregation and disruptive flow, thereby resulting in encapsulation of more than one cell into a droplet from a single cell stream.

In various embodiments, the cell concentration can be dependent on values of other tunable parameters. For example, the appropriate cell concentration can be determined based on any of 1) cell diameter, 2) inter-cell spacing, 3) microchannel width, and/or 4) microchannel height. In particular embodiments, the appropriate cell concentration is dependent on 1) cell diameter, 2) inter-cell spacing, 3) microchannel width, and/or 4) microchannel height.

In various embodiments, the concentration of cells $C_1$ in the first ordered stream of cells is defined according to Equation (1):

$$C_1\left[\frac{\text{cells}}{\text{ml}}\right] = \frac{1[\text{cells}]}{(D_1 + S_1)[\text{m}] * W_1[\text{m}] * H_1[\text{m}]} * 10^{-6}\left[\frac{\text{m}^3}{\text{mL}}\right]$$

where $D_1$ represents an average diameter of cells of the first ordered stream, $S_1$ represents spacing between pairs of cells of the first ordered stream, $W_1$ represents width of first microchannel, and $H_1$ represents height of first microchannel. Similarly, the concentration of cells $C_2$ in the second ordered stream of cells can be defined according to Equation (2):

$$C_2\left[\frac{\text{cells}}{\text{ml}}\right] = \frac{1[\text{cells}]}{(D_2 + S_2)[\text{m}] * W_2[\text{m}] * H_2[\text{m}]} * 10^{-6}\left[\frac{\text{m}^3}{\text{mL}}\right]$$

where $D_2$ represents an average diameter of cells of the second ordered stream, $S_2$ represents spacing between pairs of cells of the second ordered stream, $W_2$ represents width of the second microchannel, and $H_2$ represents height of the second microchannel.

In various embodiments, Equation (1) and Equation (2) described above refer to the maximum concentration of cells $C_1$ and maximum concentration of cells $C_2$, respectively, in their respective microchannels. In various embodiments, Equation (1) and Equation (2) described above refer to the maximum concentration of cells $C_1$ and maximum concentration of cells $C_2$, respectively, that are added to their respective wells (e.g., aqueous wells). Thus, remaining below the maximum concentration of cells $C_1$ and maximum concentration of cells $C_2$ can ensure ordering of both the first stream of cells and the second stream of cells.

In various embodiments, the concentration of cells defined in Equation (1) and Equation (2) can be adjusted according to a desired droplet diameter and volume. For example, the denominator of either Equation (1) or Equation (2) can be equal to half the volume of the desired droplet volume.

Inter-Cell Spacing

Generally, the inter-cell spacing of cells within an ordered stream influences the number of cells that are encapsulated into a single cell. As used herein, the inter-cell spacing refers to the distance between a pair of successive cells (e.g., no other cell between the pair of cells) within an ordered stream. In various embodiments, the desired inter-cell spacing of cells in an ordered stream is dependent on the volume of droplets that are formed at the junction of a microfluidic center. In various embodiments, the desired inter-cell distance between two cells is a distance that, when multiplied by the cross-sectional area of the microchannel, is between from about ¼*droplet volume to about 1*droplet volume. In various embodiments, the desired inter-cell distance between two cells is a distance that, when multiplied by the cross-sectional area of the microchannel, is between from about ½*droplet volume to about 1*droplet volume. For a square or rectangular microchannel, the cross-sectional area of the microchannel is the product of the height and width of the microchannel. For a circular microchannel, the cross-sectional area of the microchannel is the product of π and the square of the radius of the microchannel. By controlling the inter-cell spacing in this fashion, individual cells in an ordered stream of cells will be successfully encapsulated into separate, single droplets. If the inter-cell spacing is smaller than desired, then more than one cell from the ordered stream will be encapsulated in a droplet. Conversely, if the inter-cell spacing is larger than desired, many droplets will be formed that do not contain a single cell.

In various embodiments, an average inter-cell spacing between cells of a first ordered stream (e.g., in the first microchannel) and an average inter-cell spacing between cells of a second ordered stream (e.g., in the second microchannel) are substantially equal (e.g., within 10% of each other). This ensures that a cell from the first ordered stream arrives at the junction at substantially the same time as a corresponding cell from the second ordered stream, thereby resulting in co-encapsulation of the cell from the first ordered stream and the corresponding cell from the second ordered stream.

In various embodiments, cells in an ordered stream may have a distribution of inter-cell spacing. In other words, a first pair of cells in the ordered stream may have an inter-cell spacing that differs from the inter-cell spacing of a second pair of cells. In various embodiments, an average inter-cell distance of pairs of cells in an ordered stream is between from about 0.5 times the average cell diameter to about 6 times the average cell diameter. In various embodiments, pairs of successive cells in an ordered stream can independently have an inter-cell distance between from about 0.6 times the average cell diameter to about 5.5 times the average cell diameter, between from about 0.7 times the average cell diameter to about 5 times the average cell diameter, between from about 0.8 times the average cell diameter to about 4.5 times the average cell diameter, between from about 1 times the average cell diameter to about 4 times the average cell diameter, between from about 1.5 times the average cell diameter to about 3.5 times the average cell diameter, between from about 2 times the average cell diameter to about 3 times the average cell diameter, or between from about 2.25 times the average cell diameter to about 2.75 times the average cell diameter.

In various embodiments, an average inter-cell distance of pairs of cells in an ordered stream is between from about 5 μm to about 100 μm. In various embodiments, pairs of successive cells in an ordered stream can independently have an inter-cell distance between from about 6 μm to about 90 μm, between from about 7 μm to about 80 μm, between from about 8 μm to about 70 μm, between from about 9 μm to about 60 μm, between from about 10 μm to about 50 μm, between from about 11 μm to about 40 μm, between from about 12 μm to about 30 μm, or between from about 15 μm to about 20 μm.

Flow Rate

The flow rates of the aqueous phases and/or the oil phase are tunable to ensure successful ordering of cell streams and co-encapsulation of two or more cells in single droplets. As referred to herein, the first aqueous phase refers to the aqueous fluid that flows through a first microchannel carrying cells of a first cell type. The second aqueous phase refers to the aqueous fluid that flows through a second microchannel carrying cells of a second cell type. The oil phase refers to an immiscible fluid that flows through two or more microchannels to meet the first and second aqueous phase at a junction (e.g., to form single droplets).

In various embodiments, the first aqueous phase is flowed through the first microchannel at a rate between from about 5 μL/min to 100 μL/min. In various embodiments, the first aqueous phase is flowed through the first microchannel at a rate between from about 10 μL/min to 75 μL/min, between from about 15 μL/min to 50 μL/min, between from about 20 μL/min to 40 μL/min, or between from about 25 μL/min to 35 μL/min. In various embodiments, the first aqueous phase is flowed through the first microchannel at a rate between from about 10 μL/min to 40 μL/min, between from about 15 μL/min to 35 μL/min, between from about 20 L/min to 30 μL/min, or between from about 22.5 L/min to 27.5 μL/min. In various embodiments, the first aqueous phase is flowed through the first microchannel at a rate between from about 8 μL/min to 80 μL/min, between from about 10 μL/min to 60 μL/min, between from about 15 μL/min to 50 μL/min, between from about 20 μL/min to 40 μL/min, between from about 25 μL/min to 35 μL/min, or between from about 27.5 μL/min to 32.5 L/min. In various embodiments, the first aqueous phase is flowed through the first microchannel at a rate of about 60 μL/min. In various embodiments, the first aqueous phase is flowed through the first microchannel at a rate of about 45 μL/min. In various embodiments, the first aqueous phase is flowed through the first microchannel at a rate of about 30 μL/min.

In various embodiments, the second aqueous phase is flowed through the second microchannel at a rate between from about 5 μL/min to 100 μL/min. In various embodiments, the second aqueous phase is flowed through the second microchannel at a rate between from about 10 μL/min to 75 L/min, between from about 15 μL/min to 50 μL/min, between from about 20 μL/min to 40 μL/min, or between from about 25 μL/min to 35 μL/min. In various embodiments, the second aqueous phase is flowed through the second microchannel at a rate between from about 10 μL/min to 40 μL/min, between from about 15 μL/min to 35 μL/min, between from about 20 μL/min to 30 L/min, or between from about 22.5 μL/min to 27.5 μL/min. In various embodiments, the second aqueous phase is flowed through the second microchannel at a rate between from about 8 μL/min to 80 μL/min, between from about 10 μL/min to 60 μL/min, between from about 15 μL/min to 50 μL/min, between from about 20 μL/min to 40 μL/min, between from about 25 L/min to 35 μL/min, or between from about 27.5 μL/min to 32.5 L/min. In various embodiments, the second aqueous phase is flowed through the second microchannel at a rate of about 60 L/min. In various embodiments, the second aqueous phase is flowed through the second microchannel at a rate of about 45 μL/min. In various embodiments, the second aqueous phase is flowed through the second microchannel at a rate of about 30 μL/min.

In various embodiments, the first aqueous phase and the second aqueous phase are flowed through their respective microchannels at the same flow rate. In various embodiments, the first aqueous phase and the second aqueous phase are flowed through their respective microchannels at different flow rates. For example, the second aqueous phase can be flowed at a second rate that is faster than a first rate of the first aqueous phase. By flowing the second aqueous phase faster, then more cells of the second cell type that is carried by the second aqueous phase may be encapsulated in a single droplet. For example, a single droplet comprises only a single cell from the first ordered stream of cells (flowed at a first flow rate) and two or more cells from the second ordered stream of cells (flowed at a second, faster flow rate).

In various embodiments, the oil phase is flowed through an oil microchannel at a rate between from about 5 μL/min to 100 μL/min. In various embodiments, the oil phase is flowed through the oil microchannel at a rate between from about 10 μL/min to 75 μL/min, between from about 15 μL/min to 50 μL/min, between from about 20 μL/min to 40 μL/min, or between from about 25 μL/min to 35 μL/min. In various embodiments, the oil phase is flowed through the oil microchannel at a rate between from about 10 μL/min to 40 μL/min, between from about 15 μL/min to 35 μL/min, between from about 20 μL/min to 30 μL/min, or between from about 22.5 L/min to 27.5 L/min. In various embodiments, the oil phase is flowed through the oil microchannel at a rate between from about 8 μL/min to 80 μL/min, between from about 10 μL/min to 60 μL/min, between from about 15 μL/min to 50 μL/min, between from about 20 μL/min to 40 μL/min, between from about 25 μL/min to 35 μL/min, or between from about 27.5 μL/min to 32.5 μL/min. In various embodiments, the oil phase is flowed through the oil microchannel at a rate of about 60 μL/min. In various embodiments, the oil phase is flowed through the oil microchannel at a rate of about 45 L/min. In various embodiments, the oil phase is flowed through the oil microchannel at a rate of about 30 μL/min.

Ordering Cells Using Pillars

In various embodiments, microfluidic devices include additional features, such as one or more pillars, that aid in the ordering of cells into a stream. Generally, one or more pillars of a microfluidic device are useful for manipulating movement of single cells in the microfluidic device. For example, pillars can manipulate movement of single cells to ensure that the cells do not aggregate and lead to clogging of the microchannels. As another example, pillars can manipulate movement of single cells to assist in achieving a particular inter-cell spacing. This can further aid in the ordering of a stream of cells.

In various embodiments, the one or more pillars are situated at an entrance to a microchannel of the microfluidic device. For example, referring to FIG. 1A, the one or more pillars can be situated in aqueous well 105A at the entrance to the first microchannel 115A. As another example, the one or more pillars can be situated in aqueous well 105B at the entrance to the second microchannel 115B. In particular embodiments, aqueous well 105A and aqueous well 105B include one or more pillars situated at the entrance to the first microchannel 115A and second microchannel 115B, respectively. Thus, as cells in the aqueous wells 105 flow into their respective microchannels 115, the one or more pillars disrupt the flow of the cells to avoid aggregation and clumping of cells within the microchannels 115. In particular, the one or more pillars disrupt the flow of the cells to achieve a particular inter-cell spacing within the microchannels 115.

In various embodiments, one or more pillars at an entrance of a microchannel are arranged in rows. A row of pillars may be arranged substantially perpendicular or perpendicular to the flow of the cells. In various embodiments, a set of pillars includes at least 2 rows of pillars. In various embodiments, a set of pillars includes at least 3, at least 4, at least 5, at least 6, at least 7, at least 8, at least 9, at least 10, at least 15, at least 20, at least 25, at least 30, at least 35, at least 40, at least 45, or at least 50 rows of pillars.

In various embodiments, a set of pillars at an entrance of a microchannel comprise gaps between pairs of pillars. For example, a pair of pillars in the same row may have a particular gap. Generally, the gaps between pillars in rows are small enough to force cells to pass through the center of the gap, and due to laminar flow, the cells will flow into the center of the gap of the next row of pillars, and so on. In various embodiments, the gaps between a pair of pillars in a row are uniform in distance. In various embodiments, the set of pillars comprise 2 to 80 μm gaps, 3 to 60 μm gaps, 4 to 50 μm gaps, 5 to 40 μm gaps, 6 to 30 μm gaps, or 8 to 20 μm gaps between pillars. In particular embodiments, the set of pillars comprise 5 to 40 μm gaps. In various embodiments, the gaps between pairs of pillars in successive rows become successively smaller. For example, in successive rows, the gaps between pairs of pillars is between about 5% to 50% smaller than the gaps between pairs of pillars in the immediately preceding row. In some scenarios, in successive rows, the gaps between pairs of pillars is between about 10% to 40% smaller, between about 15% to about 35% smaller, between about 20% to about 30% smaller, or between about 22.5% to about 27.5% smaller than the gaps between pairs of pillars in the immediately preceding row.

In various embodiments, a row of pillars is shifted (e.g., offset) in relation to an adjacent row of pillars. Thus, through successive rows of pillars in which a row is shifted in relation to a prior row of pillars, the cells flowing through the pillars are guided in the direction of the shift towards a common point. In various embodiments, a row of pillars is shifted a proportion of the distance of a gap between a pair of pillars in the same row. For example, assuming a gap distance of X between a pair of pillars in the same row (e.g., a first row), then a second row of pillars adjacent to the first row can be shifted by a value of Z*X, where Z represents a proportion and is less than 1. In various embodiments, Z is 0.1, 0.15, 0.2, 0.25, 0.3, 0.35, 0.4, 0.45, 0.5, 0.55, 0.6, 0.65, 0.7, 0.75, 0.8, 0.85, 0.9, or 0.95.

Figure 4:
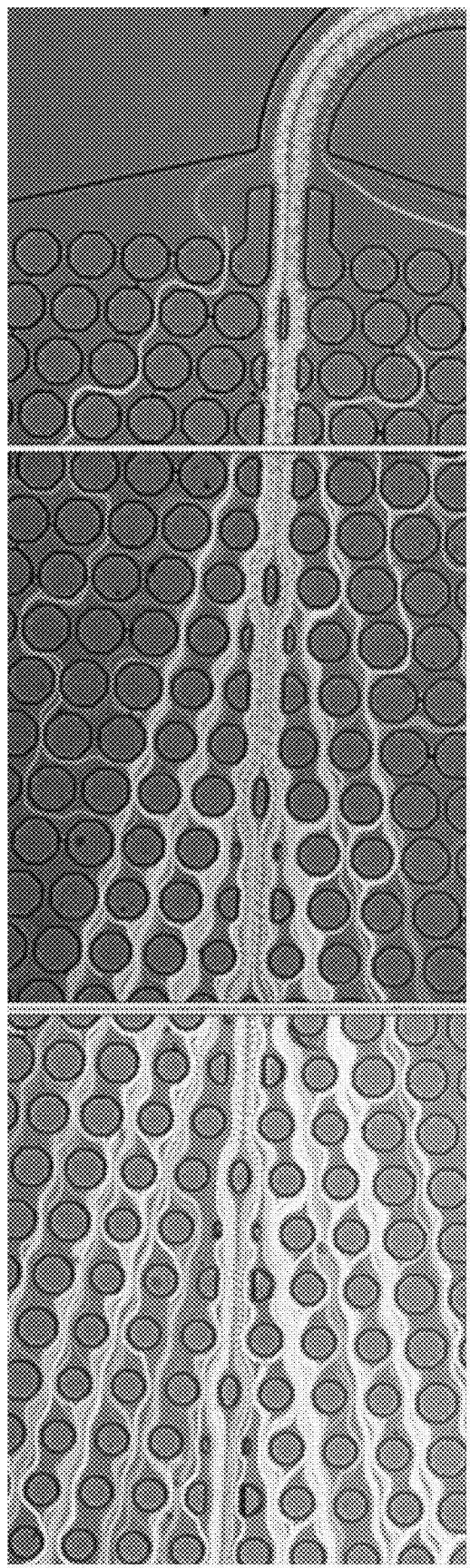
FIG. 4 shows example flow paths using pillars which separate cells into ordered streams, in accordance with an embodiment.

Reference is now made to FIG. 4, which shows example flow paths using pillars which separate cells into ordered streams, in accordance with an embodiment. Specifically, FIG. 4 shows vertically oriented rows of pillars, in which a row of pillars is shifted relative to a prior row of pillars. Here, the flow paths of the cells show that due to laminar flow, the cells are flowed through the gaps of rows of pillars to a central axis before entering into the microchannel on the right.

Encapsulating Cells of Ordered Streams into Single Droplets

Disclosed herein are methods for co-encapsulating two or more cells from two or more ordered streams into single droplets at a junction of microfluidic device. A first ordered stream of cells flows in an aqueous phase in a first microchannel to a junction, a second ordered stream of cells flows in an aqueous phase in a second microchannel to the junction, and an oil phase flows through a third microchannel to the junction. The meeting of the aqueous phases and oil phase at the junction causes the formation of single droplets.

In various embodiments, methods for co-encapsulating two or more cells involves meeting the two or more aqueous phases and the oil phase at the junction substantially simultaneously (e.g., the various phases encounter each other simultaneously or within 100 milliseconds (ms), within 10 ms, or within 1 ms). In various embodiments, methods for co-encapsulating two or more cells involves first contacting the two or more aqueous phases with one another. For example, methods may involve contacting the flowing first aqueous phase with the second aqueous phase, wherein the contacting creates a single aqueous phase comprising the first ordered stream of cells from the first aqueous phase and the second ordered stream of cells from the second aqueous phase. In various embodiments, the contacting of the flowing first aqueous phase and the second aqueous phase to create the single aqueous phase occurs at a location at or prior to the junction. As an example, reference is made to FIG. 1B, which depicts the example junction 130. Here, the first ordered stream of cells 150A flows in a first aqueous phase in the first microchannel 115A and the second ordered stream of cells 150B flows in a second aqueous phase in the second microchannel 115B. The aqueous phases of the first microchannel 115A and the second microchannel 115B meet at a location prior to the junction 130 to form a single aqueous phase.

As shown in FIG. 1B, the aqueous phases merge prior to encountering the oil phases flowing in microchannels 125A and 125B. In such embodiments, methods for co-encapsulating two or more cells further comprises contacting the flowing oil phase with the single aqueous phase to form a cone configuration within the junction. Here, the cone configuration is formed due to the immiscible oil phases interacting with the aqueous phase. Thus, single droplets are generated at the tip of the cone configuration.

In various embodiments, the oil phase is flowed to the junction at a rate between from about 5 µL/min to 100 µL/min. In various embodiments, the oil phase is flowed at a rate between from about 10 L/min to 75 µL/min, between from about 15 µL/min to 50 µL/min, between from about 20 L/min to 40 µL/min, or between from about 25 µL/min to 35 µL/min. In various embodiments, the oil phase is flowed at a rate between from about 10 µL/min to 40 µL/min, between from about 15 L/min to 35 µL/min, between from about 20 µL/min to 30 µL/min, or between from about 22.5 µL/min to 27.5 L/min.

In various embodiments, methods disclosed herein are useful for generating a population of single droplets. In various embodiments, methods involve generating at least 5, at least 10, at least 20, at least 30, at least 40, at least 50, at least 60, at least 70, at least 80, at least 90, at least 100, at least 150, at least 200, at least 300, at least 400, at least 500, at least 1000, at least 5000, at least 10,000, at least 50,000, at least 100,000, at least 500,000, at least 1 million, at least 10 million, at least 50 million, or at least 100 million single droplets. In various embodiments, methods involve generating between 10 and 10,000 single droplets. In various embodiments, methods involve generating between 50 and 5,000, between 100 and 1,000, between 200 and 900, between 300 and 800, between 400 and 700, or between 500 and 600 single droplets.

Generally, the population of single droplets is characterized by a fraction of the single droplets comprise a cell (e.g., of a first cell type) from a first ordered stream and at least one cell (e.g., of a second cell type) from a second ordered stream. The fraction of single droplets that include a cell from a first ordered stream and at least one cell from a second ordered stream exceeds a predicted fraction of single droplets comprising a cell from the first ordered stream and a cell from the second ordered stream predicted using a Poisson distribution. For example, based on Poisson's law, about 10% of single droplets would contain a cell a cell from a first ordered stream and at least one cell from a second ordered stream. The Poisson prediction is calculated by using the Poisson distribution formula, $$= Pr(X = k) = \frac{\lambda^k e^{-\lambda}}{k!},$$

where k is the number of occurrences (in this case, number of cells in each droplet), and λ is the expected value of cells in droplets. The expected value of cells in droplets is the concentration of cells divided by the volume of a droplet. As an example, given a droplet of diameter 60 µm, with 4 million cells/mL of T-cells, the Poisson formula calculates ~28% of droplets having 1 Jurkat cell. For the same droplet diameter and 9 million cells/mL of K562 cells, the Poisson formula calculates ~36% of droplets having 1 K562 cells. As these two events are independent, the number of droplets that contain a Jurkat cell and a K562 cell is 28%*36%=~10%.

In various embodiments, methods and apparati disclosed herein generate a population of single droplets characterized by a fraction of single droplets including a cell from a first ordered stream and at least one cell from a second ordered stream, wherein the fraction exceeds the predicted fraction predicted using a Poisson distribution by at least 1.5-fold. In various embodiments, the fraction exceeds the predicted fraction predicted using a Poisson distribution by at least 1.6-fold, by at least 1.7-fold, by at least 1.8-fold, by at least 1.9-fold, by at least 2.0-fold, by at least 2.1-fold, by at least 2.2-fold, by at least 2.3-fold, by at least 2.4-fold, by at least 2.5-fold, by at least 2.6-fold, by at least 2.7-fold, by at least 2.8-fold, by at least 2.9-fold, by at least 3.0-fold, by at least 3.1-fold, by at least 3.2-fold, by at least 3.3-fold, by at least 3.4-fold, by at least 3.5-fold, by at least 3.6-fold, by at least 3.7-fold, by at least 3.8-fold, by at least 3.9-fold, by at least 4.0-fold, by at least 4.1-fold, by at least 4.2-fold, by at least 4.3-fold, by at least 4.4-fold, by at least 4.5-fold, by at least 4.6-fold, by at least 4.7-fold, by at least 4.8-fold, by at least 4.9-fold, or by at least 5.0-fold.

In various embodiments, the fraction exceeds the predicted fraction predicted using a Poisson distribution by a factor ranging from 1.3-fold to 10.0-fold. In various embodiments, the fraction exceeds the predicted fraction predicted using a Poisson distribution by a factor ranging from 1.4-fold to 9.0-fold, by a factor ranging from 1.5-fold to 8.0-fold, by a factor ranging from 1.6-fold to 7.0-fold, by a factor ranging from 1.7-fold to 6.0-fold, by a factor ranging from 1.8-fold to 5.0-fold, by a factor ranging from 1.9-fold to 4.0-fold, or by a factor ranging from 2.0-fold to 3.0-fold.

Example Microfluidic Devices

Microfluidic devices, such as microfluidic devices disclosed herein, are designed and used in accordance with a range of parameters (e.g., concentration of cells in aqueous fluid, flow rate of aqueous phase including cells, flow rate of oil phase, microchannel width, and inter-cell spacing within an ordered stream of cells) to successfully achieve co-encapsulation of two or more cells in single droplets. In particular, microfluidic devices are used to find a range of flow velocities that are both fast enough for inertial focusing (e.g., to achieve ordered streams of cells), but also slow enough to achieve droplet generation. Furthermore, microfluidic devices are also designed to process cells in a high throughput manner, thereby ensuring cell viability during the process.

Tunable parameters of microfluidic devices include the width of the microfluidic channels. In particular, decreasing the width of a microchannel increases the rate of inertial focusing by decreasing the distance that cells travel to reach the equilibrium position within the microchannel. However, decreasing the microchannel width comes with the tradeoff of decreasing flow velocity by increasing the flow resistance, thereby reducing cell-processing throughput. Another tunable parameter includes the microchannel length. Specifically, the length of the channel can be tuned to allow more time for the Dean forces to inertially focus the cells. However, increasing the microchannel length also increases flow resistance, and so decreases flow velocity at a fixed operating pressure.

Disclosed herein are microfluidic devices for encapsulating pairs of cells in droplets, the microfluidic device comprising: a first microchannel, a second microchannel, and a third microchannel, wherein the first microchannel, second microchannel and third microchannel are fluidically connected to one another through a junction.

Example Junction of Microfluidic Device with Serpentine or Spiral Microchannels

Figure 5:
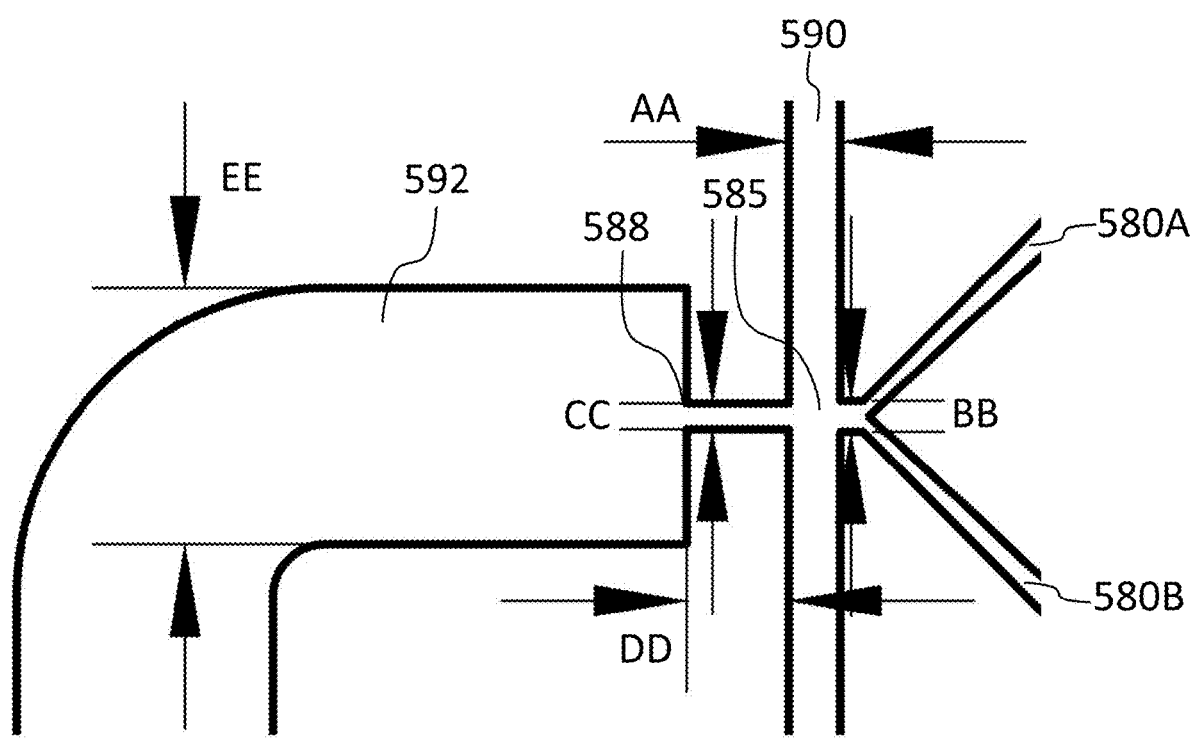
FIG. 5 depicts an example junction of a microfluidic device, in accordance with an embodiment.

Reference is made to FIG. 5, which depicts an example junction of a microfluidic device, such as an example microfluidic device including serpentine channels (as described below in reference to FIGS. 6A and 6B) or an example microfluidic device including spiral channels (as described below in reference to FIGS. 7A and 7B). Here, FIG. 5 depicts a first microchannel 580A (e.g., for carrying a first ordered stream of cells), a second microchannel 580B (e.g., for carrying a second ordered stream of cells), an oil channel 590 (for carrying an immiscible phase), a junction 585, a nozzle region 588 after the junction 585, and a post-nozzle region 592 for collecting droplets. Generally, the operation of the microfluidic device shown in FIG. 5 involves flowing solutions from the right (e.g., through first microchannel 580A and second microchannel 580B) towards the left (e.g., to the post-nozzle region 592). Additionally, FIG. 5 includes designations of the dimensions. For example, "AA" refers to the width of the oil channel 590. "BB" refers to the width of the junction 585. "CC" refers to the width of the nozzle region 588. "DD" refers to the length of the nozzle region 588. "EE" refers to the width of the post-nozzle region 592.

As shown in FIG. 5, the first microchannel 580A and second microchannel 580B may meet at the junction 585 or at a region immediately prior to the junction 585. This region then leads to the junction 585 for forming droplets. The nozzle region 588 leads away from the junction 585 to the post-nozzle region 592, which collects the formed droplets.

Referring first to the first microchannel 580A, in various embodiments, the width of the first microchannel 580A is between from about 5 µm to about 200 µm. In various embodiments, the width of the first microchannel 580A is between from about 10 µm to about 100 µm, between from about 15 µm to about 95 µm, between from about 20 µm to about 90 µm, between from about 25 µm to about 85 µm, between from about 30 µm to about 80 µm, between from about 35 µm to about 75 µm, between from about 40 µm to about 70 µm, between from about 45 µm to about 65 µm, between from about 50 µm to about 60 µm. In various embodiments, the width of the first microchannel 580A is between from about 50 µm to about 100 µm (e.g., between from about 55 µm to about 95 µm, between from about 60 µm to about 90 µm, between from about 65 µm to about 85 µm, or between from about 70 µm to about 80 µm). In various embodiments, the width of the first microchannel 580A is between from about 50 µm to about 75 µm. In particular embodiments, the width of the first microchannel 580A is about 50 µm. In particular embodiments, the width of the first microchannel 580A is about 75 µm.

In various embodiments, the width of the first microchannel 580A tapers down when approaching the junction 585. For example, the first microchannel 580A may have a first width that is located distal to the junction 585 in relation to a second width of the first microchannel 580A that is located more proximal to the junction 585. The first width of the first microchannel 580A may be greater than the second width of the first microchannel 580A. In various embodiments, the first width of the first microchannel 580A (e.g., located distal to the junction 585) is between from about 40 µm to about 100 µm, between from about 45 µm to about 80 µm, or between from about 50 µm to about 60 µm. In particular embodiments, the first width of the first microchannel 580A (e.g., located distal to the junction 585) is about 50 µm. In various embodiments, the second width of the first microchannel 580A (e.g., located proximal to the junction 585) is between from about 10 µm to about 40 µm, between from about 20 µm to about 35 µm, or between from about 25 µm to about 32 µm. In particular embodiments, the second width of the first microchannel 580A (e.g., located proximal to the junction 585) is about 30 µm. In particular embodiments, the second width of the first microchannel 580A (e.g., located proximal to the junction 585) is about 25 µm. In particular embodiments, the width of the first microchannel 580A tapers down from a first width of 50 µm to a second width of 30 µm at the junction 585.

In various embodiments, the width of the second microchannel 580B is between from about 5 µm to about 200 µm. In various embodiments, the width of the second microchannel 580B is between from about 10 µm to about 100 µm, between from about 15 µm to about 95 µm, between from about 20 µm to about 90 µm, between from about 25 µm to about 85 µm, between from about 30 µm to about 80 µm, between from about 35 µm to about 75 µm, between from about 40 µm to about 70 µm, between from about 45 µm to about 65 µm, between from about 50 µm to about 60 µm. In various embodiments, the width of the second microchannel 580B is between from about 50 µm to about 100 µm (e.g., between from about 55 µm to about 95 µm, between from about 60 µm to about 90 µm, between from about 65 µm to about 85 µm, or between from about 70 µm to about 80 µm). In various embodiments, the width of the second microchannel 580B is between from about 50 µm to about 75 µm. In particular embodiments, the width of the second microchannel 580B is about 50 µm. In particular embodiments, the width of the second microchannel 580B is about 75 µm.

In various embodiments, the width of the second microchannel 580B tapers down when approaching the junction 585. For example, the second microchannel 580B may have a first width that is located distal to the junction 585 in relation to a second width of the second microchannel 580B that is located more proximal to the junction 585. The first width of the second microchannel 580B may be greater than the second width of the second microchannel 580B. In various embodiments, the first width of the second microchannel 580B (e.g., located distal to the junction 585) is between from about 40 µm to about 100 µm, between from about 45 µm to about 80 µm, or between from about 50 µm to about 60 µm. In particular embodiments, the first width of the second microchannel 580B (e.g., located distal to the junction 585) is about 50 µm. In various embodiments, the second width of the second microchannel 580B (e.g., located proximal to the junction 585) is between from about 10 µm to about 40 µm, between from about 20 µm to about 35 µm, or between from about 25 µm to about 32 µm. In particular embodiments, the second width of the second microchannel 580B (e.g., located proximal to the junction 585) is about 30 µm. In particular embodiments, the second width of the second microchannel 580B (e.g., located proximal to the junction 585) is about 25 µm. In particular embodiments, the width of the second microchannel 580B tapers down from a first width of 50 µm to a second width of 30 µm at the junction 585.

In various embodiments, the width of the oil microchannel 590 (denoted as "AA" in FIG. 5) is between from about 5 µm to about 200 µm. In various embodiments, the width of the oil microchannel 590 is between from about 10 µm to about 150 µm, between from about 20 µm to about 140 µm, between from about 30 µm to about 130 µm, between from about 40 µm to about 125 µm, between from about 50 µm to about 120 µm, between from about 60 µm to about 75 µm, between from about 40 µm to about 70 µm, between from about 45 µm to about 65 µm, between from about 50 µm to about 60 µm. In various embodiments, the width of the oil microchannel 590 is between from about 50 µm to about 100 µm (e.g., between from about 55 µm to about 95 µm, between from about 60 µm to about 90 µm, between from about 65 µm to about 85 µm, or between from about 70 µm to about 80 µm). In various embodiments, the width of the oil microchannel 590 is between from about 50 µm to about 75 µm. In particular embodiments, the width of the oil microchannel 590 is about 50 µm. In particular embodiments, the width of the oil microchannel 590 is about 60 µm. In particular embodiments, the width of the oil microchannel 590 is about 75 µm.

Referring next to the junction 585, in various embodiments, the width of the junction 585 (denoted as "BB" in FIG. 5) is between from about 5 µm to about 200 µm. In various embodiments, the width of the junction 585 is between from about 10 µm to about 150 µm, between from about 20 µm to about 140 µm, between from about 30 µm to about 130 µm, between from about 40 µm to about 125 µm, between from about 50 µm to about 120 µm, between from about 60 µm to about 75 µm, between from about 40 µm to about 70 µm, between from about 45 µm to about 65 µm, between from about 50 µm to about 60 µm. In various embodiments, the width of the junction 585 is between from about 50 µm to about 100 µm (e.g., between from about 55 µm to about 95 µm, between from about 60 µm to about 90 µm, between from about 65 µm to about 85 µm, or between from about 70 µm to about 80 µm). In various embodiments, the width of the junction 585 is between from about 50 µm to about 75 µm. In particular embodiments, the width of the junction 585 is about 50 µm. In particular embodiments, the width of the junction 585 is about 60 µm. In particular embodiments, the width of the junction 585 is about 75 µm.

In various embodiments, a ratio between the width of the oil channel 590 (denoted as "AA" in FIG. 5) and the width of the junction 585 (denoted as "BB" in FIG. 5) is between from about 1 to about 5. In various embodiments, the ratio between the width of the oil channel 590 (denoted as "AA" in FIG. 5) and the width of the junction 585 (denoted as "BB" in FIG. 5) is between from about 1 to about 4, between from about 1 to about 3, from about 1 to about 2, between from about 2 to about 4, or between from about 2 to about 3. In particular embodiments, the ratio between the width of the oil channel 590 (denoted as "AA" in FIG. 5) and the width of the junction 585 (denoted as "BB" in FIG. 5) is about 100 µm/60 µm (e.g., about 1.6).

Referring next to the width of the nozzle 588, the width (denoted as "CC" in FIG. 5) can be designed to control the size of resulting droplets. In various embodiments, the width of the nozzle 588 controls the size of the resulting droplets by about +20 µm, centered around the nozzle width. For example, given a width of a nozzle of 50 µm, the resulting droplets are sized between 30-70 µm (e.g., depending on the pressure applied to the aqueous channels and their corresponding flow rates). In various embodiments, the width of the nozzle 588 is between from about 5 µm to about 200 µm. In various embodiments, the width of the nozzle 588 is between from about 10 µm to about 150 µm, between from about 20 µm to about 140 µm, between from about 30 µm to about 130 µm, between from about 40 µm to about 125 µm, between from about 50 µm to about 120 µm, between from about 60 µm to about 75 µm, between from about 40 µm to about 70 µm, between from about 45 µm to about 65 µm, between from about 50 µm to about 60 µm. In various embodiments, the width of the nozzle 588 is between from about 50 µm to about 75 µm. In particular embodiments, the width of the nozzle 588 is about 50 µm. In particular embodiments, the width of the nozzle 588. In particular embodiments, the width of the nozzle 588 is about 75 µm. In particular embodiments, the width of the nozzle 588 is about 100 µm.

In particular embodiments, the width of the nozzle 588 (denoted as "CC" in FIG. 5) is less than the width of the junction 585 (denoted as "BB" in FIG. 5). In various embodiments, the width of the nozzle 588 is at least 1% less than the width of the junction 585. In various embodiments, the width of the nozzle 588 is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% less than the width of the junction 585. In some embodiments, the width of the nozzle 558 is between from about 40 µm to about 55 µm and the width of the junction 585 is between from about 55 µm to about 75 µm. In some embodiments, the width of the nozzle 558 is between from about 45 µm to about 52 µm and the width of the junction 585 is between from about 58 µm to about 65 µm. In some embodiments, the width of the nozzle 558 is about 50 µm and the width of the junction 585 is about 60 µm.

Referring next to the length of the nozzle 588, the length of the nozzle 588 (denoted as "DD" in FIG. 5) can be designed to ensure droplet formation at higher flow rates of aqueous and/or oil phases. For example, higher flow velocities or flow rates may result in an aqueous/oil interface that is in a co-flow or jetting regime, which prevents the formation of single droplets. Therefore, increasing the length of the nozzle 588 can enable the increase of flow rates to higher values while still allowing droplet formation to occur. In various embodiments, the length of the nozzle 588 is between from about 20 µm to about 500 µm. In various embodiments, the length of the nozzle 588 is between from about 30 µm to about 450 µm, is between from about 40 µm to about 400 µm, is between from about 50 µm to about 350 µm, is between from about 75 µm to about 300 µm, is between from about 100 µm to about 250 µm, or is between from about 150 µm to about 225 µm. In particular embodiments, the length of the nozzle 588 is about 50 µm. In particular embodiments, the length of the nozzle 588 is about 200 µm.

Referring next to post-nozzle region 592, the width of the post-nozzle region 592 (denoted as "EE" in FIG. 5) can be designed to ensure that droplets have sufficient space to form without merging into each other. In various embodiments, the width of the post-nozzle region 592 is between from about 50 µm to about 1000 µm. In various embodiments, the width of the post-nozzle region 592 is between from about 100 µm to about 900 µm, between from about 150 µm to about 850 µm, between from about 200 µm to about 800 µm, between from about 250 µm to about 750 µm, between from about 300 µm to about 700 µm, between from about 350 µm to about 650 µm, between from about 400 µm to about 600 µm, between from about 450 µm to about 550 µm, or between from about 475 µm to about 525 µm. In particular embodiments, the width of the post-nozzle region 592 is about 500 µm.

In various embodiments, the width of the junction 585 (denoted as "BB" in FIG. 5) is greater than the width of nozzle 588 (denoted as "CC" in FIG. 5). In various embodiments, a ratio between the width of the junction 585 (denoted as "BB" in FIG. 5) and the width of nozzle 588 (denoted as "CC" in FIG. 5) is between from about 1 to about 5. In various embodiments, the ratio between the width of the junction 585 and the width of nozzle 588 is between from about 1 to about 4, between from about 1 to about 3, from about 1 to about 2, between from about 2 to about 4, or between from about 2 to about 3. In particular embodiments, the ratio between the width of the junction 585 and the width of nozzle 588 is about 60 µm/50 µm (e.g., about 1.2).

In various embodiments, the width of the post-nozzle region 592 (denoted as "EE" in FIG. 5) is greater than the width of the nozzle 588 (denoted as "CC" in FIG. 5). In various embodiments, a ratio of the width of the post-nozzle region 592 (denoted as "EE" in FIG. 5) to the width of the nozzle 588 (denoted as "CC" in FIG. 5) is between from about 1 to about 15. In various embodiments, a ratio of the width of the post-nozzle region 592 (denoted as "EE" in FIG. 5) to the width of the nozzle 588 (denoted as "CC" in FIG. 5) is between from about 2 to about 14.5, between from about 3 to about 14, between from about 4 to about 13.5, between from about 5 to about 13, between from about 6 to about 12.5, between from about 7 to about 12, between from about 8 to about 11.5, or between about 9 to about 11. In particular embodiments, a ratio of the width of the post-nozzle region 592 to the width of the nozzle 588 is about 10.

Serpentine Microchannel Microfluidic Device

FIG. 6A depicts the example microfluidic device with serpentine microchannels. For purposes of introduction, the microfluidic device includes two aqueous wells 610A and 610B. Here, cells of a first cell type can be introduced in aqueous fluid into aqueous well 610A and cells of a second cell type can be introduced in aqueous fluid into aqueous well 610B.

Figure 6B:
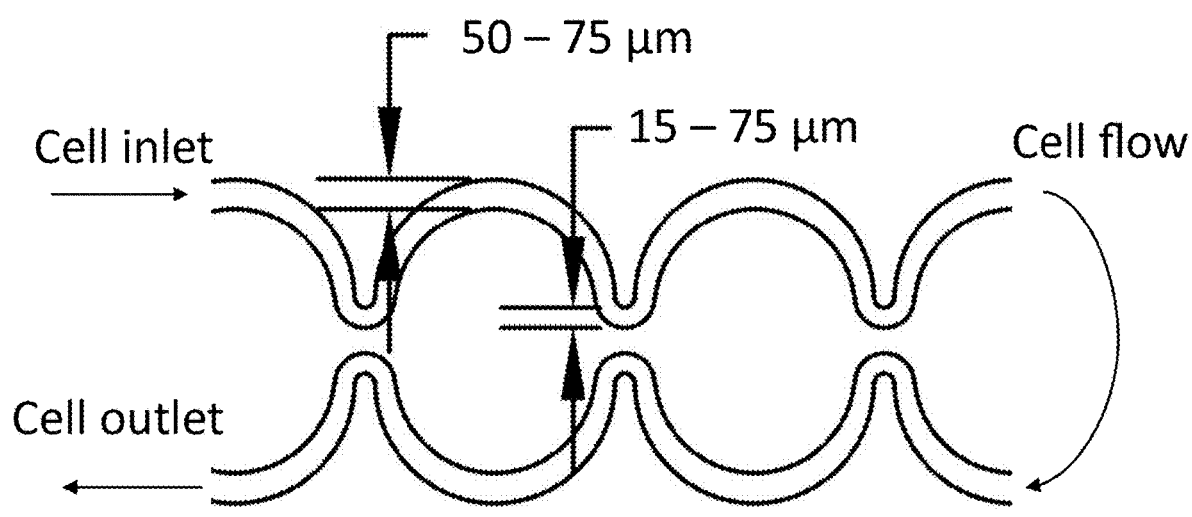
FIG. 6B depicts an example curved region of a serpentine microchannel of the example microfluidic device shown in FIG. 6A at a higher magnification.

As shown in FIG. 6A, the aqueous well 610A is fluidically connected to a curved region 615A of a first serpentine microchannel. Similarly, the aqueous well 610B is fluidically connected to a curved region 615B of a second serpentine microchannel. Thus, cells provided through aqueous well 610A flow back and forth through the curved region 615A of the serpentine microchannel to the junction 640. The curved region 615A imparts inertial focusing forces to order the stream of cells before they arrive at the junction 640, as is shown in FIG. 1B. Similarly, cells provided through aqueous well 610B flow back and forth through the curved region 615B of the serpentine microchannel to the junction 640. The curved region 615B imparts inertial focusing forces to order the stream of cells before they arrive at the junction 640, as is shown in FIG. 1B. Reference is now made to FIG. 6B, which depicts an example curved region of a serpentine microchannel of the example microfluidic device shown in FIG. 6A at a higher magnification. Specifically, FIG. 6B shows the inset 650 shown in FIG. 6A at a higher magnification. Here, the inset 650 shows the directional flow of the cells beginning at the cell inlet along the serpentine microchannel with asymmetric curves. Inset 650 shows that the cells enter through the cell inlet and flow through asymmetric curves. Specifically, the curved region includes multiple undulating portions which impart the inertial focusing forces on the cells. In this particular example, an undulating portion may have a channel width of 0.075 mm, followed by a narrowing down to a channel width of 0.050 mm. Here, the radius of curvature of the channel at the channel width of 0.075 mm is larger than the radius of curvature of the channel at the channel width of 0.05 mm. The cells continue to flow, as indicated by the directional arrow of "cell flow," through additional undulations to the "cell outlet." Generally, the directional flow of the cells through the top undulations is from left to right, whereas the directional flow of the cells through the bottom undulations is from right to left. Thus, the continued back and forth flow of the cells through undulating portions results in the ordering of the stream of cells. Returning to FIG. 6A, there may be even further undulations in which the cells further flow e.g., from left to right and/or from right to left, such that the inertial focusing forces imparted on the cells through these even further undulations further order the cells within the microchannel. In the particular example microfluidic device shown in FIG. 6A, cells in aqueous well 610A flowed from right to left through a first set of undulating portions, then flowed from left to right through a second set of undulating portions, then flowed from right to left through a third set of undulating portions, then flowed from left to right through a fourth set of undulating portions, and then flowed from right to left through a fifth (and final) set of undulating portions to the junction 640. Similarly, cells in aqueous well 610B flowed from right to left through a first set of undulating portions, then flowed from left to right through a second set of undulating portions, then flowed from right to left through a third set of undulating portions, then flowed from left to right through a fourth set of undulating portions, and then flowed from right to left through a fifth (and final) set of undulating portions to the junction 640.

Additionally shown in FIG. 6A is an oil well 625 in which an oil phase is introduced to the microfluidic device. The oil phase flows from the oil well 625 through microchannel 630 to the junction 640. At the junction 640, the first ordered stream of cells originating from well 610A, the second stream of cells originating from well 610B, and the oil phase from oil well 625 combine to form single droplets that encapsulate two or more cells. An exemplary image at the junction 640 during co-encapsulation is shown in FIG. 1B.

Spiral Microchannel Microfluidic Device

FIG. 7A depicts an example microfluidic device with spiral microchannels. For purposes of introduction, the microfluidic device includes two aqueous wells 710A and 710B. Here, cells of a first cell type can be introduced in aqueous fluid into aqueous well 710A and cells of a second cell type can be introduced in aqueous fluid into aqueous well 710B. Generally, the operation of the microfluidic device shown in FIG. 7A involves flowing solutions from the left (e.g., from wells 710A, 710B and 725) towards the right (e.g., to the junction 740 and towards the collection well 745).

As shown in FIG. 7A, the aqueous well 710A is fluidically connected to a curved region 715A of a first spiral microchannel. Similarly, the aqueous well 710B is fluidically connected to a curved region 715B of a second spiral microchannel. Thus, cells provided through aqueous well 710A flow through the curved region 715A of the spiral microchannel to the junction 740. The curved region 715A imparts inertial focusing forces to order the stream of cells before they arrive at the junction 740. Similarly, cells provided through aqueous well 710B flow through the curved region 715B of the spiral microchannel to the junction 740. The curved region 715B imparts inertial focusing forces to order the stream of cells before they arrive at the junction 740.

Figure 7B:
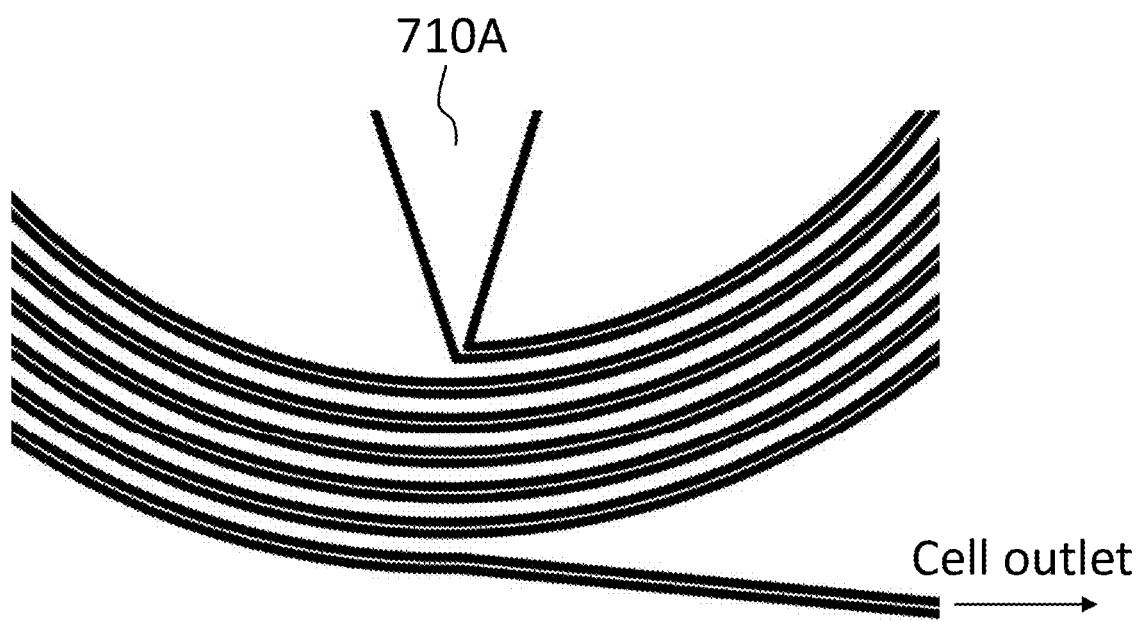
FIG. 7B depicts an example curved region of a spiral microchannel of the example microfluidic device shown in FIG. 7A at a higher magnification.

Reference is now made to FIG. 7B depicts an example curved region of a spiral microchannel of the example microfluidic device shown in FIG. 7A at a higher magnification. Specifically, FIG. 7B shows the inset 750 shown in FIG. 7A at a higher magnification. Here, the inset 750 shows the spiral microchannel as it loops around with continuously increasing radius of curvature. In this particular example, the radius of curvature of the microchannel closer to the aqueous well 710A is smaller than the radius of curvature of the microchannel closer to the cell outlet shown in FIG. 7B. Thus, as the cells flow through the spiral microchannel, the inertial focusing forces imparted on the cells causes the organization of the cells into an ordered stream of cells.

Additionally shown in FIG. 7A is an oil well 725 in which an oil phase is introduced to the microfluidic device. The oil phase flows from the oil well 725 through microchannel 730 to the junction 740. At the junction 740, the first ordered stream of cells originating from well 710A, the second stream of cells originating from well 710B, and the oil phase from oil well 725 were combined to form single droplets that encapsulate two or more cells.

Additional Features of Microfluidic Devices

In various embodiments, microfluidic devices disclosed herein, such as microfluidic devices shown in FIG. 6A and/or FIG. 7A can include additional features for improving the ordering of streams of cells and/or co-encapsulation of two or more cells in single droplets.

In various embodiments, an additional feature includes one or more or pillars. The pillars can be useful for guiding the flow of cells from the aqueous well 115A and/or aqueous well 115B into the respective microchannels. For example, a set of pillars can be helpful for establishing the inter-cell distance in the two ordered stream of cells. Thus, given appropriate inter-cell distance in the two ordered streams of cells, two or more cells are successfully co-encapsulated into single droplets at the junction.

In various embodiments, a set of pillars is located at an entrance to a microchannel. For example, referring again to FIG. 1A, the set of pillar may be located at the entrance of microchannel 115A or microchannel 115B. In particular embodiments, the set of pillars may be located at the end of the aqueous channel 105A or 105B immediately prior to the entrance to the microchannel 115A and microchannel 115B. In various embodiments, the set of pillars comprise 5 to 40 µm gaps between pillars. The example flow of cells around a set of pillars is shown in FIG. 4.

High Throughput Cell-Cell Interaction Assays

As described herein, methods involve co-encapsulating two or more cells in a single droplet for performing high-throughput cell-cell interaction assays. In particular, a method for performing an assay in a single droplet comprising two cells can include the steps of: flowing a first aqueous phase comprising a first ordered stream of cells in a first microchannel towards a junction; flowing a second aqueous phase comprising a second ordered stream of cells in a second microchannel towards the junction; flowing an oil phase in a third microchannel towards the junction; and at the junction, generating the single droplet formed from the first aqueous phase, the second aqueous phase, and the oil phase, the single droplet comprising a cell from the first ordered stream of cells and a cell from the second ordered stream of cells.

In various embodiments, to perform the cell-cell interaction assays, one or more reagents for performing cell-cell interaction assays can be introduced into single droplets. For example, reagents can be introduced via the first aqueous phase and/or the second aqueous phase. Thus, by co-encapsulating the two or more cells in a single droplet, the reagents are simultaneously encapsulated in the single droplet. Generally, reagents are useful for indicating the presence of an interaction between the two or more cells. Thus, using the reagents, methods involve detecting an interaction within the single droplet between the two or more cells. For example, the reagents can be used to detect a biomarker analyte indicative of the interaction. Such a biomarker analyte can be any of an antibody, cytokine, cytolytic proteins, hormones, and/or small molecules (e.g. less than 2 kDa or 1 kDa).

In various embodiments, reagents indicative of an interaction between two or more cells can be fluorescent markers, beads, nucleic acid barcodes, or a combination thereof. In various embodiments, a bead (or a particle), may include, for example, polystyrene, polyethylene, or any other suitable polymer. In some cases, the particle may be a polymer-coated particle such as polystyrene coated gold particle, polyethylene coated silica particle etc. In some embodiments, the particle may be a gel particle or a hydrogel particle. The particle may be spherical or nonspecial, and may be of any suitable size, e.g., less than about 10 micrometers, less than about 3 micrometers, less than about 1 micrometer, less than about 300 nm, less than about 100 nm, etc. In some cases, the particle may be modified to promote attachment of antibodies or other agents to the surface of the particle. For instance, in one set of embodiments, the particle may be coated with streptavidin and the antibody modified with a biotinylated portion that can bind to the streptavidin, thereby immobilizing the antibody relative to the surface of the particle.

In some embodiments, the particles capture and detect a particular biomarker analytes. For example, a particle can be coated with an antibody exhibiting affinity for a target biomarker analyte. Such a particle can, in various embodiments, be a streptavidin coated polystyrene bead that is coated with biotinylated capture antibody. Additionally, a detection antibody is tagged with a signaling entity (e.g., a fluorescent label). The biomarker analyte, if present due to an interaction between two or more cells in the single droplet, attaches to the capture bead and the detection antibody upon contact. The biomarker analyte is thus captured onto the bead with the labeled detection antibody further concentrating around the bead. This provides sufficient signal (e.g., at a sufficient signal to noise ratio) to enable detection of the signaling entity, thereby indicating that a cell-cell interaction has occurred.

In some cases, the particles may be able to capture and detect several different biomarker analytes simultaneously (e.g., molecules secreted or otherwise released by one or more of the co-encapsulated cells). For example, the capture particles can be coated with a first antibody specific for a first antigen and a second antibody specific for a second antigen. As a specific non-limiting example, the droplets can include the capture particle with both the first antibody and the second antibody, two or more cells, and labeled antibodies specific for the first antigen labeled with a first signaling entity (e.g., a fluorescent red dye) and labeled antibodies specific for the second antigen with a second signaling entity (e.g., a fluorescent green dye). Thus, if an interaction between the two or more cells occurs, resulting in the release of the first antigen and second antigen, the particles can capture both the first antigen and the second antigen. Then, the labeled antibodies labeled with the first signaling entity and labeled antibodies labeled with the second signaling entity concentrate around the capture particle (due to the bound first and second antigen), thereby enabling detection of the signal arising from the first and second signaling entities. Further details and methods for performing cell-cell interaction assays are described in WO2017165791, which is incorporated by reference in its entirety.

In various embodiments, bead-based, in-droplet barcoding can be implemented by including a barcoding polystyrene bead or spherical hydrogel during drop formation. Further details of barcoded beads are described in US20150298091, which is incorporated by reference in its entirety. This allows next-generation sequencing of many cells while maintaining the association between cells that were encapsulated in the same drop.

Co-Encapsulated Cells

Embodiments described herein involve performing assays in single droplets comprising two or more cells. In various embodiments, the two or more cells may interact with each other, thereby resulting in a change one or more markers, such as markers expressed by one of the two or more cells and/or markers secreted into the environment around the two or more cells.

As described herein, methods involve co-encapsulating the two or more cells into single droplets by providing a first ordered stream of cells of a first cell type and a second ordered stream of cells of a second cell type. By tuning various parameters, a single cell of the first cell type and one or more cells of the second cell type can be successfully encapsulated into the single droplet. In various embodiments, the cell from the first ordered stream of cells and the one or more cells from the second ordered stream of cells are of the same cell type. In various embodiments, the cell from the first ordered stream of cells and the one or more cells from the second ordered stream of cells are different cells (e.g., of different cell types).

In various embodiments, the cell of a first cell type from the first ordered stream of cells is an effector cell. An example of an effector cell is an immune cell, such as a B-cell, a T-cell, a natural killer cell, a lymphocyte, a macrophage, a neutrophil, a basophil, or a mast cell. In particular embodiments, the cell of a first cell type is a B-cell. In particular embodiments, the cell of the first cell type is a T-cell. For example, the T-cell may be a cytotoxic CD8+ T-cell. As another example, the T-cell may be a CD4+ T-cell. In various embodiments, the effector cell may be genetically modified or engineered. For example, the effector cell may be a T cell having a genetically-modified T cell receptor. For instance, in some cases, a T-cell may be taken from a subject (e.g., healthy or diseased), and modified to include a chimeric antigen receptor. The T-cells may be expanded, then assayed as discussed herein to determine target cells that the modified T-cells react to.

In various embodiments, the cell of the second cell type from the second ordered stream of cells is a cell that may interact with a cell of the first cell type (e.g., effector cell). In particular embodiments, the cell of the second cell type is an antigen presenting cell (APC). Example APCs include macrophages, microglia, dendritic cells, B cells (e.g., memory B cells), tumor cells or any native or modified cells. Thus, by co-encapsulating effector cells (e.g., a T-cell) with APCs in single droplets, high through-put screening can be performed to identify interactions between certain T-cells and certain APCs.

In various embodiments, cells of the first type (e.g., effector cells) may interact with cells of a second type by producing or secreting antibodies, cytokines, or cytolytic proteins, or other compounds (e.g., perforins, granzymes, etc.). Other compounds that could be secreted include other gene-encoded proteins or other compounds that are not proteins, e.g., penicillin, hormones, small molecules (e.g. less than 2 kDa or 1 kDa). In various embodiments, the interaction between the cell of a first cell type (e.g., effector cell) and the cell of a second cell type (e.g., APC) may be direct (e.g., the effector cell binds directly to the APC), and/or indirect. As non-limiting examples, T-cells and APCs from a cancer patient could be studied to determine those receptors on the T-cells that are able to recognize tumor antigen presented by APCs. Further details of example cells (e.g., effector cells) for performing cell-cell interaction assays are described in WO2017165791, which is incorporated by reference in its entirety.

Example System Embodiments

Additionally described herein are systems and devices for performing the assays in droplets comprising two cells. An example system can include a microfluidic device, such as an example microfluidic device described herein. In various embodiments, the system may also include one or more of: (a) one or more pumps or control modules for controlling the flow of aqueous fluids and/or oil phase in the microfluidic device, (b) a temperature control module for controlling the temperature of one or more portions of the subject devices and/or droplets therein and which is operably connected to the microfluidic device(s), and/or (c) a detection module, i.e., a detector, e.g., an optical or fluorescent imager, operably connected to the microfluidic device(s). The one or more detection modules i.e., a detector, e.g., an optical or fluorescent imager, are configured for detecting the presence of signal (e.g., signal from reagents indicative of a cell-cell interaction) within one or more droplets. In some embodiments, detector modules are configured to recognize one or more components of one or more droplets, in one or more flow channels.

EXAMPLES

Example 1: Serpentine Channels of a Microfluidic Device Successfully Order and Encapsulate Pairs of Cells into Droplets A microfluidic device with serpentine microchannels was developed and fabricated for ordering and co-encapsulating pairs of cells into single droplets. Specifically, a microfluidic device in accordance with FIG. 6A was fabricated. Generally, the operation of the microfluidic device shown in FIG. 6A involves flowing solutions from the right (e.g., from wells 610A, 610B and 625) towards the left (e.g., to the junction 640 and towards the collection well 645).

The channel width of the serpentine microchannels for ordering streams of cells were between 50 μm to 75 μm. Specifically, channel width of a smaller undulating portion was 50 μm, as is shown in FIG. 6B. The channel width of a larger undulating portion was 75 μm at the apex, as shown in FIG. 6B, before going down to 50 μm where it meets the smaller undulation portion.

Cells of a first cell type (e.g., T-cells) were loaded into aqueous well 610A at a concentration of 4 million cells/milliliter. The average cell diameter of cells of the first cell type was 8 μm. Cells of a second cell type (e.g., antigen-presenting cells, and specifically K562 cells engineered to be antigen-presenting cells) were loaded into aqueous well 610B at a concentration of 9 million cells/milliliter. The average cell diameter of cells of the second cell type was 15 μm.

The aqueous pressure applied to aqueous well 610A and 610B was 1450 mbar. The T-cells provided through aqueous well 610A flowed back and forth through the curved region 615A of the serpentine microchannel to the junction 640. The curved region 615A imparted inertial focusing forces to order the stream of T-cells before they arrived at the junction 640. Similarly, K-562 cells engineered to be APCs provided through aqueous well 610B flow back and forth through the curved region 615B of the serpentine microchannel to the junction 640. The curved region 615B imparted inertial focusing forces to order the stream of K-562 cells before they arrived at the junction 640. The pressure applied to the oil well was 1200 mbar. The T-cells and K-562 cells underwent co-encapsulation at the junction 640.

Figure 8:
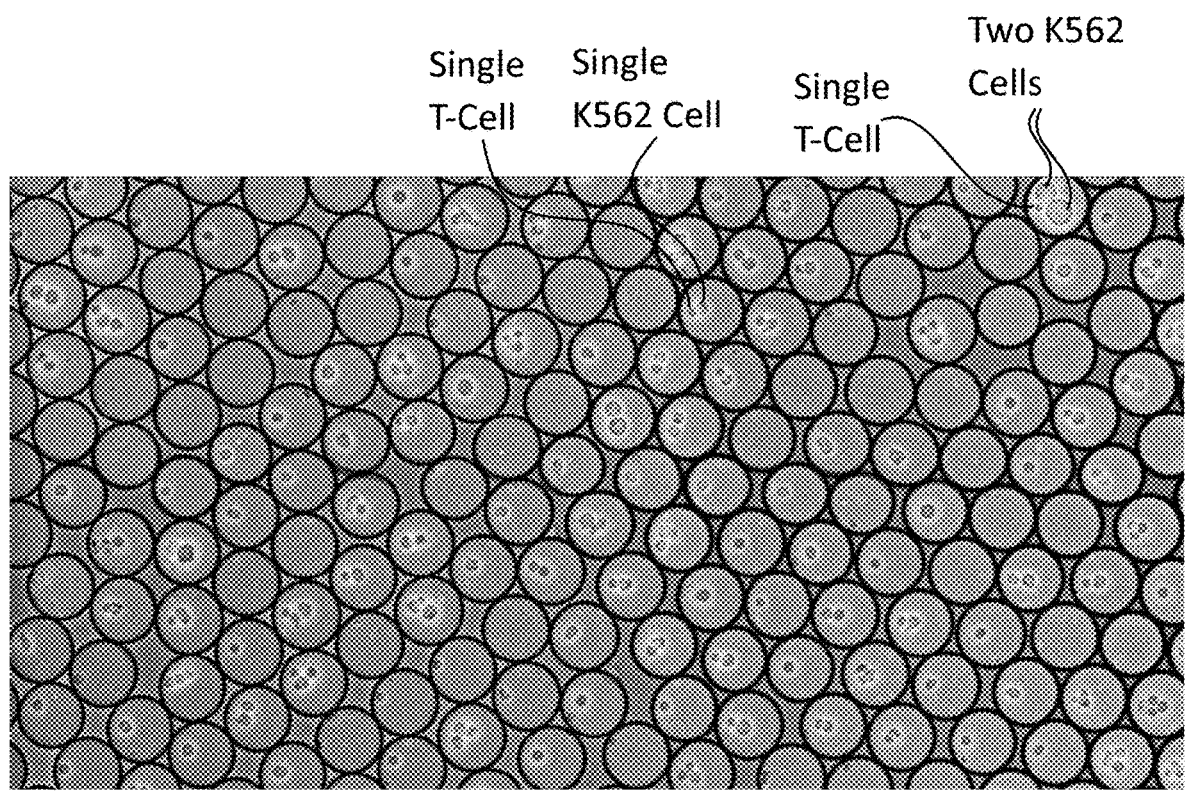
FIG. 8 shows successful loading of two different cells in single droplets, in accordance with an embodiment.

FIG. 8 shows successful loading of two different cells (e.g., T-cells and K-562 cells engineered to be antigen-presenting cells) in single droplets. Single droplets were able to successfully encapsulate T-cells and K-562 cells either at a 1:1 ratio or a 1:2 ratio (as labeled in FIG. 8). Generally, in the microfluidic device shown in FIG. 6A, approximately 26% of all droplets have a 1:1 ratio of T-cells and K562 cells.

At these cell concentrations, Poisson's Law predicts only 10% of droplets would contain cells at a 1:1 ratio. Thus, the efficiency results shown in FIG. 8 represents an advancement beyond Poisson's Law by at least 2.5 fold.

Example 2: Characterization of Ordered Stream of Cells

Using the microfluidic device described in Example 1, an analysis was performed to determine characteristics of an ordered stream of cells. In particular, the analysis was performed to determine the inter-cell distances (e.g., distance between successive cells within an ordered stream) that would lead to successful co-encapsulation of cells from two separate ordered streams.

An ordered stream of cells was generated by flowing cells through a curved region of a serpentine channel. Prior to the ordered stream of cells entering the junction, bright field pictures of the ordered stream of cells were captured, and inter-cell distances of successive cells within an ordered stream were measured. FIG. 9A shows an example brightfield image captured of two ordered streams of cells. An example inter-cell distance is labeled.

Figure 9B:
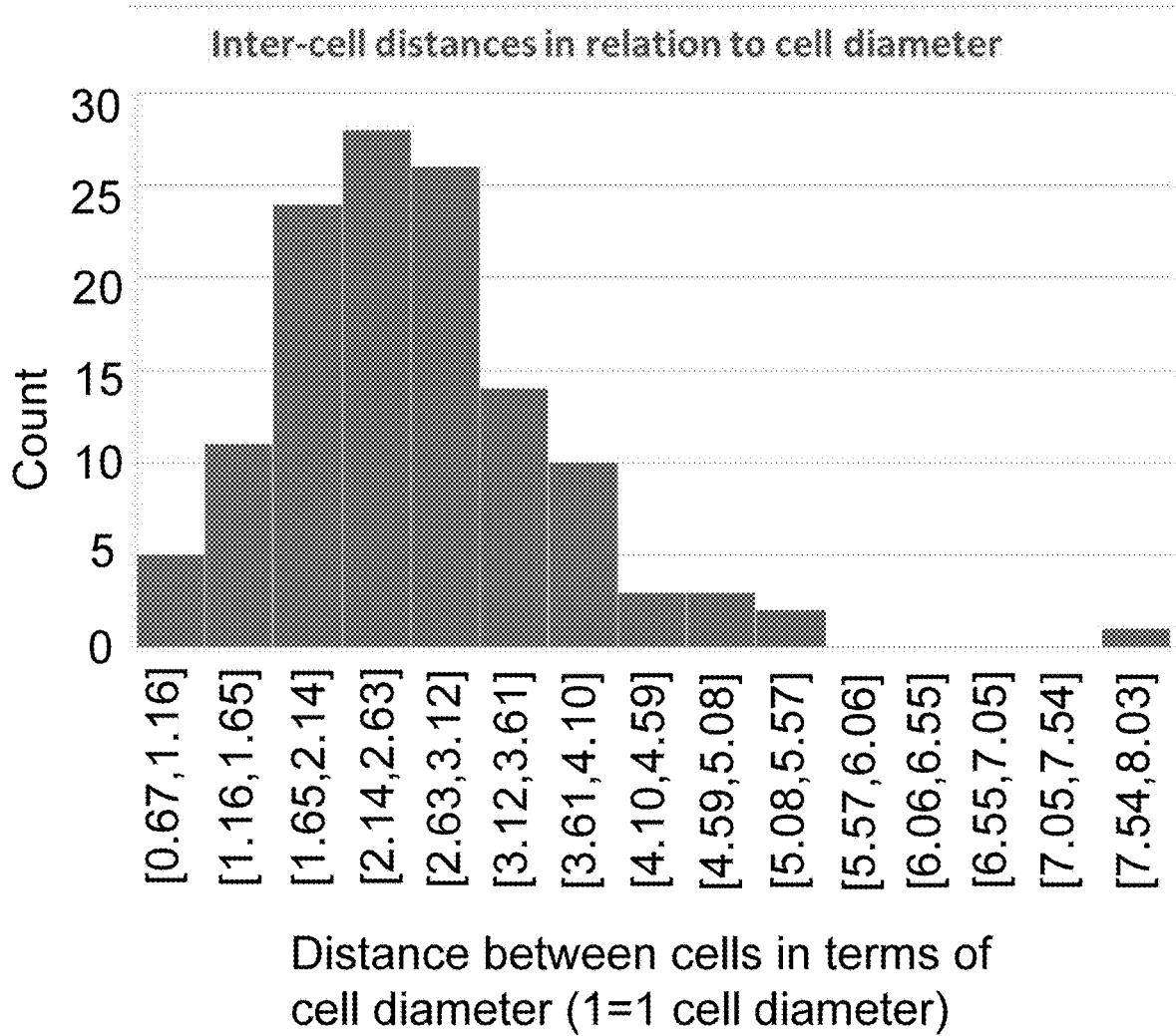
FIG. 9B shows example inter-cell distances relative to cell diameter for cells in an ordered stream.

FIG. 9B shows a distribution of the example inter-cell distances relative to cell diameter for cells in an ordered stream (e.g., an average cell diameter of 8μ). In particular the majority of cells exhibited inter-cell distances between 1 to 4 times the cell diameter, with some inter-cell distances ranging up to ~5.5 times an average cell diameter. Table 1 below further shows the standard deviation of inter-cell spacings of successively paired cells. In general, the standard deviation of inter-cell spacings of cells is less than 10 μm.

TABLE 1

Calculated inter-cell spacings across various numbers of cells.

| Number of Pairs of Cells (Total number of cells) | Standard Deviation of Inter-cell spacings of Paired Cells |
|---|---|
| 10 (11 total cells) | 6.14 μm |
| 20 (21 total cells) | 7.19 μm |
| 30 (31 total cells) | 7.43 μm |
| 40 (41 total cells) | 7.04 μm |
| 50 (51 total cells) | 6.99 μm |
| 60 (61 total cells) | 7.28 μm |
| 70 (71 total cells) | 7.07 μm |
| 80 (81 total cells) | 8.66 μm |
| 90 (91 total cells) | 8.33 μm |
| 100 (101 total cells) | 8.34 μm |
| 110 (111 total cells) | 8.25 μm |
| 120 (121 total cells) | 8.42 μm |

Example 3: Example Cell-Cell Assay within a Single Droplet

An experiment was undertaken to co-encapsulate single Jurkat cells (T-cells) with single K562 cells engineered to be APCs. Jurkat cells were first stained with a bi-specific antibody that binds to the cell surface of Jurkat cells, and further binds to IL-2 cytokines. IL-2 represents an activation cytokine that is released by activated Jurkat cells. Excess bi-specific antibody is washed away, and then a second fluorescent detection antibody (e.g., red fluorescence) is added to the cell mixture. This fluorescently-labeled detection antibody binds to IL-2 cytokines only.

Using the microfluidic device described in Example 1, a mixture of the fluorescent detection antibody and Jurkat cells were provided to a first aqueous well and infused through a first microchannel of the microfluidic device. K562 cells engineered to be APCs were provided to a second aqueous well and infused through a second microchannel of the microfluidic device. Individual Jurkat cells and K562 cells were co-encapsulated into single droplets. The fluorescent detection antibody was also encapsulated into single droplets with the cells.

Figure 10:
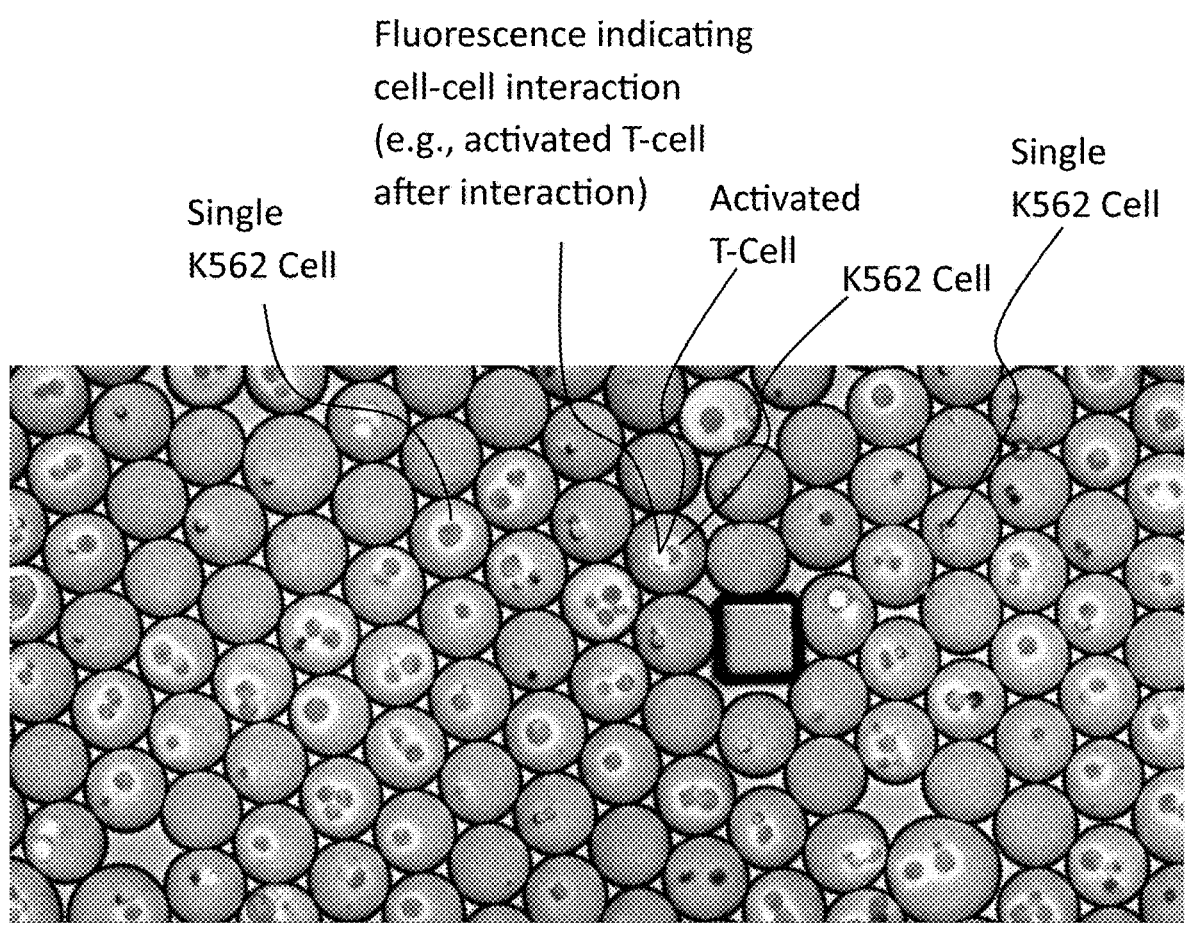
FIG. 10 shows co-encapsulated Jurkat T cells and K562 cells in single droplets for performing a cell-cell interaction assay.

FIG. 10 shows co-encapsulated Jurkat T cells and K562 cells in single droplets for performing a cell-cell interaction assay. As shown in FIG. 10, single Jurkat cells are fluorescently labeled as blue, whereas single K562 cells are fluorescently labeled as green. Activated Jurkat T cells secrete IL-2 which attached to the bi-specific antibody on the Jurkat cell surface. The fluorescent detection antibody further attached to the other side of the IL-2, thus bringing the red fluorophore to the surface of the cell. As shown in FIG. 10, the fluorescence indicating cell-cell interaction was detectable (in this case, red fluorescence). Thus, activated Jurkat T-cells were detected via presence of this fluorescence indicating cell-cell interaction.

Figure 11:
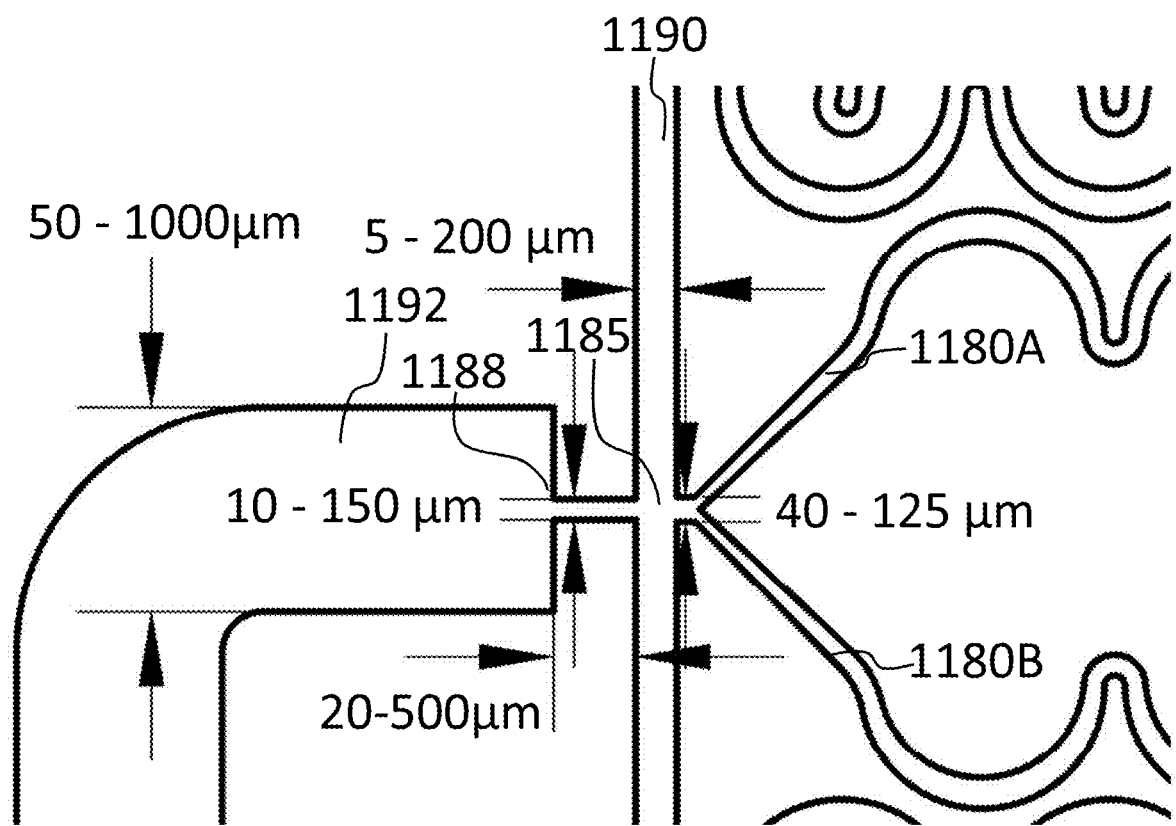
FIG. 11 depicts dimensions of an exemplary microfluidic device.

Example 4: Additional Exemplary Microfluidic Device Successfully Orders and Encapsulates Pairs of Cells into Droplets An additional microfluidic device with serpentine microchannels was developed and fabricated for ordering and co-encapsulating pairs of cells into single droplets. Specifically, a microfluidic device in accordance with the serpentine channels shown in FIG. 6A was fabricated. FIG. 11 further depicts dimensions at a junction of the exemplary microfluidic device.

In particular, the dimensions at the junction of the exemplary microfluidic device include the following:
  Width of first microchannel 1180A tapers from 50 μm down to 30 μm at the junction 1185
  Width of second microchannel 1180B tapers from 50 μm down to 30 μm at the junction 1185
  Width of junction 1185 is 60 μm
  Width of oil microchannel 1190 is 100 μm
  Length of nozzle 1188 is 200 μm
  Width of nozzle 1188 is 50 μm
  Width of post-nozzle region 1192 is 500 μm
  Ratio of width of nozzle 1188 to width of post-nozzle region 1192 is 50 μm to 500 μm (e.g., 1 to 10).
  Ratio of width of the oil channel 1190 to the width of the junction 1185 is 100 μm to 60 μm (e.g., ratio of 5 to 3).

The microfluidic device was tested for ultra high-throughput generation of paired cell droplets. In particular, the microfluidic device achieved generation of paired cell droplets at a rate of at least 8,000 droplets per second, and even reached 10,000 droplets per second depending on droplet size. For example, for droplets of approximately 60 μm, the device achieved droplet generation at 6,600 droplets per second. For droplets of approximately 55 μm, the device achieved droplet generation at 8,000 droplets per second.

Figures 12A, 12B:
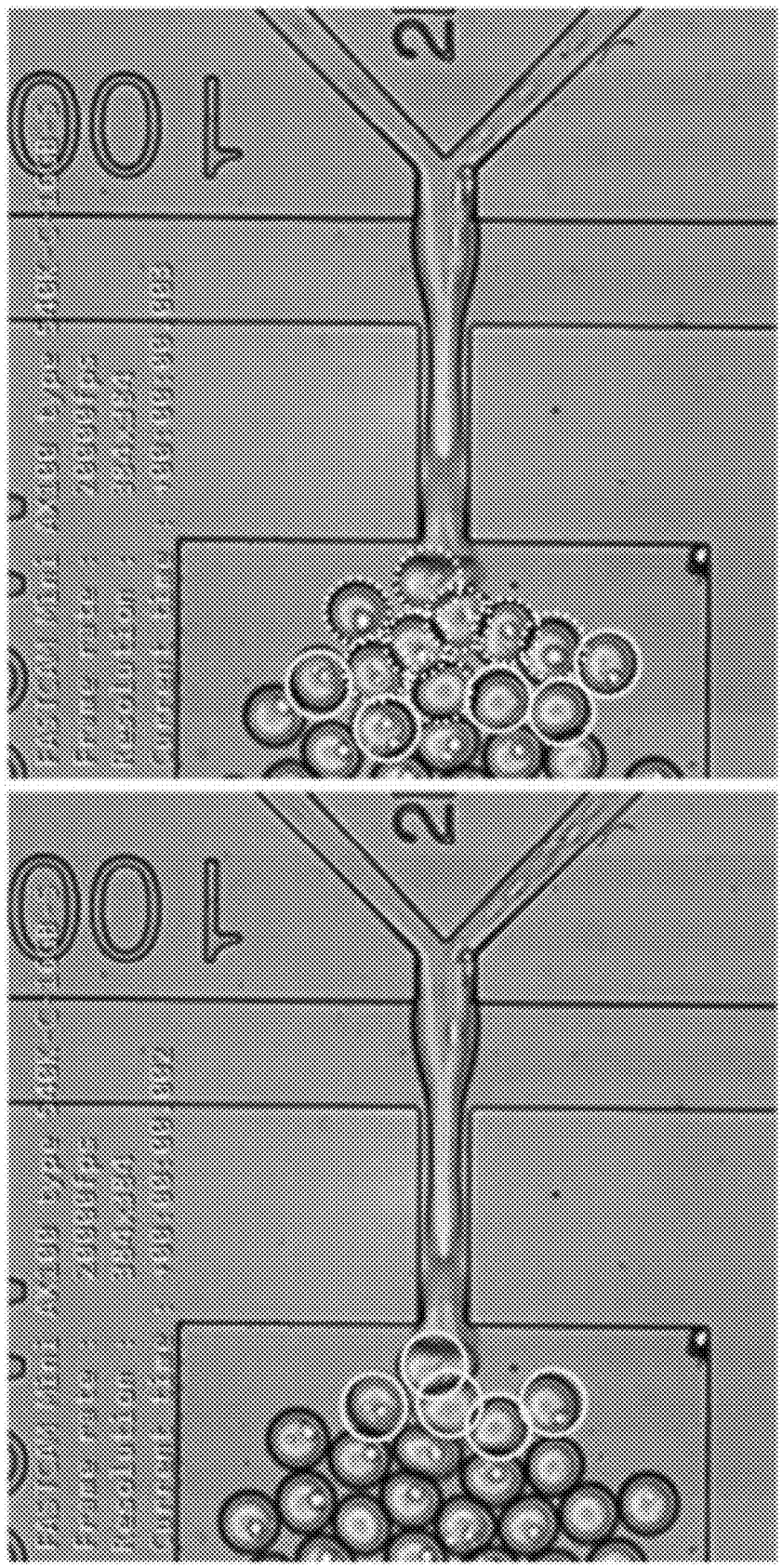
FIG. 12A depicts a video still of formation of droplets within the exemplary microfluidic device at a time of 2 ms. Five droplets are circled in solid line.
FIG. 12B depicts a video still of formation of droplets within the exemplary microfluidic device at a time of 3 ms (e.g., 1 ms after the video still shown in FIG. 12A). The five droplets originally shown in FIG. 12A are additionally shown in FIG. 12B and circled via solid lines. An additional eight droplets are shown circled in dotted lines.

Specifically, FIG. 12A depicts a video still of formation of droplets within the exemplary microfluidic device at a time of 2 ms. Five droplets are circled in solid line. FIG. 12B depicts a video still of formation of droplets within the exemplary microfluidic device at a time of 3 ms (e.g., 1 ms after the video still shown in FIG. 12A). The five droplets originally shown in FIG. 12A are additionally shown in FIG. 12B and circled via solid lines. An additional eight droplets are shown circled in dotted lines. Therefore, the droplet generation rate is 8 droplets per millisecond, or 8,000 droplets per second.

Figure 13:
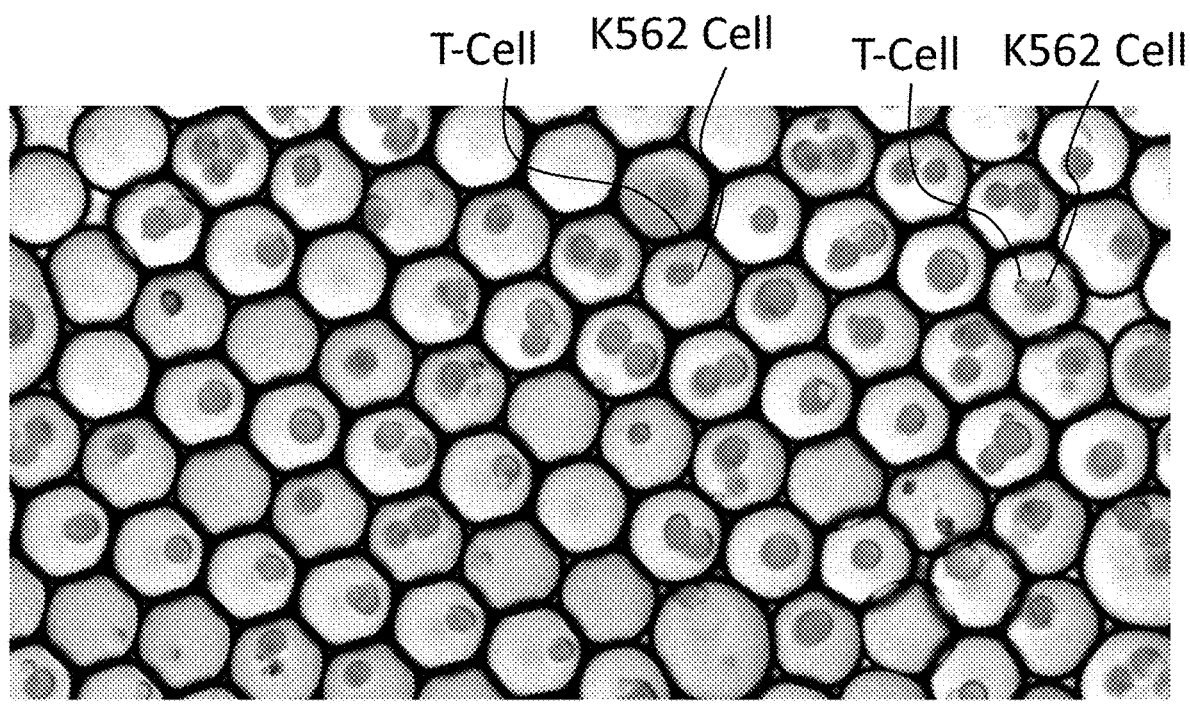
FIG. 13 depicts paired-cell droplets including paired T-cells and K562 cells, which function as antigen-presenting cells (APCs).

FIG. 13 depicts paired-cell droplets including paired T-cells and K562 cells, which function as antigen-presenting cells (APCs). Altogether, approximately 30% of all droplets have 1 T-cell paired with at least one K562 cell. This exceeds the predicted fraction predicted using a Poisson distribution by about 3-fold.

What is claimed is:

1. A method for encapsulating a population of single droplets, the method comprising:
   flowing a first aqueous phase comprising a first ordered stream of immune cells in a first microchannel towards a junction, the first microchannel comprising between 60 to 120 undulating portions, wherein each of the 60 to 120 undulating portions comprises at least a 90 degree change in a flow vector across a length of each undulating portion of the first channel;
   flowing a second aqueous phase comprising a second ordered stream of antigen presenting cells (APCs) in a second microchannel towards the junction, the second microchannel comprising between 60 to 120 undulating portions, wherein each of the 60 to 120 undulating portions comprises at least a 90 degree change in a flow vector across a length of each undulating portion of the second channel;
   flowing an oil phase in a third microchannel towards the junction; and
   at the junction formed at a meeting of the first microchannel, the second microchannel, and the third microchannel, generating the population of single droplets formed from the first aqueous phase, the second aqueous phase, and the oil phase, the population of single droplets includes a total number of single droplets in the population of single droplets, wherein each single droplet of the total number of single droplets comprises only one immune cell from the first ordered stream of immune cells and an APC from the second ordered stream of APCs, and wherein the total number of single droplets in the population of single droplets exceeds a predicted number of single droplets comprising only one immune cell from the first ordered stream and an APC from the second ordered stream predicted using a Poisson distribution.

2. The method of claim 1, wherein the method generates droplets of the population of single droplets at a rate of at least 5,000 droplets per second.

3. The method of claim 1, wherein each of the 60 to 120 undulating portions of the first microchannel comprises at least a 180 degree change in a flow vector across the length of each undulation portion of the first channel.

4. The method of claim 1, wherein each of the 60 to 120 undulating portions of the second microchannel comprises at least a 180 degree change in a flow vector across the length of each undulation portion of the second channel.

5. The method of claim 1, further comprising:
   flowing the population of single droplets away from the junction through a nozzle region of a nozzle connected to the junction, and the nozzle region having a width smaller than a width of the junction; and flowing the population of single droplets through the nozzle region to a post-nozzle region connected to an end of the nozzle, and the post-nozzle region having a width greater than the width of the nozzle region.

6. The method of claim 5, wherein the width of the nozzle region is between 10 μm to 150 μm, and wherein a length of the nozzle region is between 20 μm to 500 μm.

7. The method of claim 5, wherein the width of the nozzle region is about 60 μm and wherein a length of the nozzle region is about 50 μm.

8. The method of claim 5, wherein the width of the post-nozzle region is between 50 μm to 1000 μm.

9. The method of claim 8, wherein the width of the post-nozzle region is about 300 μm.

10. The method of claim 1, wherein the 60 to 120 undulating portions of the first microchannel impart inertial focusing forces on cells of the first ordered stream of cells.

11. The method of claim 1, wherein the first microchannel tapers down from a first width between 40 μm to 100 μm to a second width between 10 μm to 40 μm as the first microchannel approaches the junction.

12. The method of claim 11, wherein the first microchannel tapers down from a first width of about 50 μm to a second width of about 30 μm as the first microchannel approaches the junction.

13. The method of claim 1, wherein the second microchannel tapers down from a first width between 40 μm to 100 μm to a second width between 10 μm to 40 μm as the second microchannel approaches the junction.

14. The method of claim 13, wherein the second microchannel tapers down from a first width of about 50 μm to a second width of about 30 μm as the second microchannel approaches the junction.

15. The method of claim 1, wherein a width of the junction is between 40 μm to 125 μm.

16. The method of claim 1, wherein a width of the junction is about 80 μm.

17. The method of claim 1, wherein a width of the third microchannel is between 5 μm to 200 μm.

18. The method of claim 1, wherein an inter-cell spacing of at least 80% of cells in the first ordered stream of immune cells or the second ordered stream of APCs is between 1 times an average cell diameter and 3.5 times an average cell diameter of the immune cells and APCs, respectively.

* * * * *